United States Patent
Pan et al.

(10) Patent No.: US 11,676,682 B1
(45) Date of Patent: Jun. 13, 2023

(54) METHODS FOR ACCURATE SEQUENCE DATA AND MODIFIED BASE POSITION DETERMINATION

(71) Applicant: Industrial Technology Research Institute, Hsinchu (TW)

(72) Inventors: Chao-Chi Pan, Hsinchu (TW); Jenn-Yeh Fann, Hsinchu County (TW); Chung-Fan Chiou, Cyonglin Township (TW); Hung-Chi Chien, Hsinchu (TW); Hui-Ling Chen, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 814 days.

(21) Appl. No.: 16/672,232

(22) Filed: Nov. 1, 2019

Related U.S. Application Data

(62) Division of application No. 15/659,585, filed on Jul. 25, 2017, now Pat. No. 10,515,714, which is a
(Continued)

(51) Int. Cl.
*C12Q 1/68* (2018.01)
*C12Q 1/6869* (2018.01)
*G16B 30/00* (2019.01)

(52) U.S. Cl.
CPC ............ *G16B 30/00* (2019.02); *C12Q 1/6869* (2013.01)

(58) Field of Classification Search
CPC ...... G16B 30/10; G16B 30/00; C12Q 1/6869; C12Q 2531/125; C12Q 2537/165
See application file for complete search history.

(56) References Cited

U.S. PATENT DOCUMENTS

| 4,264,731 A | 4/1981 | Shine |
| 6,087,099 A | 7/2000 | Gupte et al. |
(Continued)

FOREIGN PATENT DOCUMENTS

| EP | 0 653 489 A1 | 5/1995 |
| JP | 2003-514514 | 4/2003 |
(Continued)

OTHER PUBLICATIONS

Pacific Biosciences Substantive Motion 1 (For Rescinding the Benefit Afforded to Junior Party ITRI) in Patent Interference No. 105,970 (RT), dated Mar. 12, 2014.
(Continued)

*Primary Examiner* — Sang H Nguyen
(74) *Attorney, Agent, or Firm* — Finnegan, Henderson, Farabow, Garrett & Dunner, LLP

(57) ABSTRACT

Disclosed herein are methods of determining the sequence and/or positions of modified bases in a nucleic acid sample present in a circular molecule with a nucleic acid insert of known sequence comprising obtaining sequence data of at least two insert-sample units. In some embodiments, the methods comprise obtaining sequence data using circular pair-locked molecules. In some embodiments, the methods comprise calculating scores of sequences of the nucleic acid inserts by comparing the sequences to the known sequence of the nucleic acid insert, and accepting or rejecting repeats of the sequence of the nucleic acid sample according to the scores of one or both of the sequences of the inserts immediately upstream or downstream of the repeats of the sequence of the nucleic acid sample.

36 Claims, 17 Drawing Sheets

Specification includes a Sequence Listing.

Related U.S. Application Data division of application No. 14/286,904, filed on May 23, 2014, now Pat. No. 9,747,414, which is a division of application No. 13/889,298, filed on May 7, 2013, now abandoned, which is a division of application No. 13/492,593, filed on Jun. 8, 2012, now abandoned, which is a division of application No. 12/613,291, filed on Nov. 5, 2009, now Pat. No. 8,486,630.

(60) Provisional application No. 61/167,313, filed on Apr. 7, 2009, provisional application No. 61/112,548, filed on Nov. 7, 2008.

(56) References Cited

U.S. PATENT DOCUMENTS

| | | | |
|---|---|---|---|
| 6,218,152 B1 * | 4/2001 | Auerbach | C12N 15/10 |
| | | | 536/23.1 |
| 6,274,320 B1 | 8/2001 | Rothberg et al. | |
| 6,764,835 B2 * | 7/2004 | Short | C12N 15/1027 |
| | | | 435/69.7 |
| 7,244,559 B2 | 7/2007 | Rothberg et al. | |
| 7,282,337 B1 | 10/2007 | Harris | |
| 7,302,146 B2 | 11/2007 | Turner et al. | |
| 7,399,614 B2 | 7/2008 | Zon | |
| 8,153,375 B2 | 4/2012 | Travers et al. | |
| 9,767,251 B2 * | 9/2017 | Pan | G16B 30/10 |
| 2001/0039039 A1 | 11/2001 | Weissman et al. | |
| 2002/0182630 A1 | 12/2002 | Milosavljevic | |
| 2004/0248161 A1 | 12/2004 | Rothberg et al. | |
| 2005/0142559 A1 | 6/2005 | Makrigiorgos | |
| 2006/0024711 A1 | 2/2006 | Lapidus et al. | |
| 2006/0061754 A1 | 3/2006 | Turner et al. | |
| 2007/0020640 A1 | 1/2007 | McCloskey et al. | |
| 2007/0231808 A1 | 10/2007 | Gouda et al. | |
| 2007/0287151 A1 | 12/2007 | Linnarsson | |
| 2009/0280538 A1 | 11/2009 | Patel et al. | |
| 2009/0298075 A1 | 12/2009 | Travers et al. | |
| 2010/0121582 A1 | 5/2010 | Pan et al. | |
| 2010/0221716 A1 | 9/2010 | Flusberg et al. | |
| 2012/0295260 A1 | 11/2012 | Pan et al. | |
| 2013/0029853 A1 | 1/2013 | Flusberg et al. | |
| 2015/0379194 A1 | 12/2015 | Pan et al. | |

FOREIGN PATENT DOCUMENTS

| | | |
|---|---|---|
| JP | 2003-515149 | 4/2003 |
| JP | 2005-505748 | 2/2005 |
| JP | 2007-530020 | 11/2007 |
| WO | WO 01/38580 | 5/2001 |
| WO | WO 2007/106509 | 9/2007 |
| WO | WO 2009/017678 | 2/2009 |
| WO | WO 2009/120372 | 10/2009 |

OTHER PUBLICATIONS

Pacific Biosciences Substantive Motion 2 (For Judgment Based on Invalidity under 35 U.S.C. § 103) in Patent Interference No. 105,970 (RT), dated Mar. 12, 2014.
Sorenson et al., U.S. Appl. No. 61/201,551, filed Dec. 11, 2008.
Travers et al., U.S. Appl. No. 61/099,696, filed Sep. 24, 2008.
Patel et al., U.S. Appl. No. 61/072,160, filed Mar. 28, 2008.
Declaration of Gerald Zon, Ph.D., with Exhibit A, dated Mar. 5, 2014.
Gupta, "Single-molecule DNA sequencing technologies for future genomics research," *Trends in Biotechnology*, 26: 602-611 (2008).
Declaration of Dr. Stephen Turner Pursuant to 37 C.F.R. § 1.132, dated Mar. 6, 2014.
Declaration of Dr. Stephen Turner Pursuant to 37 C.F.R. § 1.132, dated Dec. 4, 2013, Submitted During Prosecution of U.S. Appl. No. 13/930,178.
Brock et al., *Biology of Microorganisms*, 7th Edition, p. 870, Prentice Hall, Englewood Cliffs, NJ (1994).
Industrial Research Technology Institute Opposition 1 in Patent Interference No. 105,970 (RT), dated May 9, 2014.
Industrial Research Technology Institute Opposition 2 in Patent Interference No. 105,970 (RT), dated May 9, 2014.
Pacific Biosciences Opposition 2 in Patent Interference No. 105,970 (RT), dated May 9, 2014.
Industrial Research Technology Institute Reply 2 in Patent Interference No. 105,970 (RT), dated Jun. 13, 2014.
Pacific Biosciences Reply 1 in Patent Interference No. 105,970 (RT), dated Jun. 13, 2014.
Pacific Biosciences Reply 2 in Patent Interference No. 105,970 (RT), dated Jun. 13, 2014.
"Determine." *Dictionary.com Unabridged*. Random House, Inc. May 9, 2014. <Dictionary.com http://dictionary.reference.com/browse/determine>.
First Declaration of Gerald Zon, Ph.D. in Support of Pacific Biosciences' Opposition 2, executed May 8, 2014.
Second Declaration of Gerald Zon, Ph.D. in Support of Pacific Biosciences' Opposition 2, executed May 7, 2014.
Declaration of Stephen M. Moore in Patent Interference No. 105,970 (RT) dated Jun. 11, 2014.
Slides 1-61 of Pacific Biosciences' Cold Spring Harbor Personal Genomes Meeting Presentation (Oct. 12, 2008).
Third Declaration of Shawn Levy, Ph.D. in Patent Interference No. 105,970 (RT) dated May 9, 2014.
Bentley et al., "Accurate whole human genome sequencing using reversible terminator chemistry," *Nature*, 456: 53-59 (2008) and Supplemental Information, pp. 1-55.
Horton et al., "Recombinant DNA Technology," *Principles of Biochemistry*, pp. 735-742 (Third Edition, 2002).
Mardis, "Next-Generation DNA Sequencing Methods," *Annual Review of Genomics and Human Genetics*, 9: 387-402 (2008).
Mertz et al., "Cleavage of DNA by $R_I$ Restriction Endonuclease Generates Cohesive Ends," *Proceedings of the National Academy of Sciences*, 69(11): 3370-3374 (1972).
Paull et al., "The 3' to 5' Exonuclease Activity of Mre11 Facilitates Repair of DNA Double-Strand Break," *Molecular Cell*, 1: 969-979 (1998).
Sambrook, "Fragmentation of DNA by nebulization," (Abstract), *Cold Spring Harbor Protocols* (2006).
Shendure et al., "Next-generation DNA sequencing," *Nature Biotechnology*, 26(10): 1135-1145 (2008).
Fourth Declaration of Shawn Levy, Ph.D. in Patent Interference No. 105,970 (RT) dated May 9, 2014.
Office Action dated May 21, 2014, for U.S. Appl. No. 13/492,593.
Reply to Office Action dated Aug. 15, 2014, for U.S. Appl. No. 13/492,593.
Judgment Bd.R. 127 in Patent Interference No. 105,970 (JGN), dated Aug. 3, 2014.
Decision on Motions 37 C.F.R. § 41.125 in Patent Interference No. 105,970 (JGN), dated Sep. 3, 2014.
Miner et al., "Molecular barcodes detect redundancy and contamination in hairpin-bisulfite PCR," Nucleic Acids Research, 32(17): e135 (4 pages) (2004).
Extended European Search Report and Preliminary Opinion for European Patent Application No. 14150163.5, dated Jul. 22, 2014, (10 pages).
The European Bioinformatics Institute European Nucleotide Archive annotated/assembled sequences User Manual, Release 116, Jun. 2013.
Office Action dated Sep. 30, 2014, for U.S. Appl. No. 13/889,298.
Reply to Office Action under 37 C.F.R. § 1.111 dated Dec. 12, 2014, for U.S. Appl. No. 13/889,298.
Final Office Action dated Oct. 20, 2014, for U.S. Appl. No. 13/492,593.
Office Action dated Nov. 21, 2014, for U.S. Appl. No. 13/492,593.
Reply to Office Action dated Feb. 5, 2015, for U.S. Appl. No. 13/492,593 (31 pages).
Final Office Action dated Feb. 20, 2015, for U.S. Appl. No. 13/889,298, (8 pages).
Applicant-Initiated Interview Summary in U.S. Appl. No. 13/889,298 dated Apr. 22, 2015, (3 pages).

(56) References Cited

OTHER PUBLICATIONS

Final Office Action dated Apr. 20, 2015, for U.S. Appl. No. 13/492,593, (7 pages).
Brief of Appellant Industrial Technology Research Institute in Patent Interference No. 105,970, dated Mar. 19, 2015 (177 pages).
Appellee's Brief in Patent Interference No. 105,970, dated May 15, 2015 (74 pages).
Office Action in U.S. Appl. No. 14/717,996 dated Aug. 8, 2016, (11 pages).
Response to Office Action dated Nov. 8, 2016, for U.S. Appl. No. 14/717,996 (8 pages).
Adessi et al., "Solid Phase DNA Amplification: Characterisation of Primer Attachment and Amplification Mechanisms," *Nucleic Acids Research*, vol. 28, No. 20 e87, pp. 1-8 (2000).
Branton et al., "The Potential and Challenges of Nanopore Sequencing," *Nat Biotechnol.*, vol. 26, pp. 1146-1153 (Oct. 2008).
Braslavsky et al., "Sequence Information Can Be Obtained From Single DNA Molecules," *PNAS*, vol. 100, pp. 3960-3964 (2003).
Brenner et al., "Gene Expression Analysis by Massively Parallel Signature Sequencing (MPSS) on Microbead Arrays," *Nature Biotechnology*, vol. 18, pp. 630-634 (2000).
Brown, "Mutation, Repair, and Recombination," Genomes Second Edition, Chapter 14, pp. 418-457 (2002), John Wiley & Sons, New York.
Chen et al., "DNA Cleavage in Trans By the Active Site Tyrosine During FLP Recombination: Switching Protein Partners Before Exchanging Strands," *Cell*, vol. 69, pp. 647-658 (1992).
Eid et al. "Real-Time DNA Sequencing From Single Polymerase Molecules," *Science*, vol. 323, pp. 133-138 (2009).
Guo et al., "Weakening of the T7 Promoter-Polymerase Interaction Facilitates Promoter Release," *The Journal of Biological Chemistry*, vol. 280, pp. 14956-14961 (2005).
Harris et al., "Single-Molecule DNA Sequencing of a Viral Genome," *Science*, vol. 320, pp. 106-109 (Apr. 2008).
Kato, "Impact of the Next Generation DNA Sequencers," *Int J Clin Exp Med*, vol. 2, pp. 193-202 (Jul. 2009).
Korlach et al., "Selective Aluminum Passivation for Targeted Immobilization of Single DNA Polymerase Molecules in Zero-Mode Waveguide Nanostructures," *Proc. Natl. Acad. Sci. USA*, vol. 105, pp. 1176-1181 (Jan. 2008).
Laird et al., "Hairpin-Bisulfite PCR: Assessing Epigenetic Methylation Patterns on Complementary Strands of Individual DNA Molecules," *Proc. Natl. Acad. Sci. USA*, vol. 101, pp. 204-209 (2004).
Levene et al., "Zero-Mode Waveguides for Single-Molecule Analysis at High Concentrations," *Science*, vol. 299, pp. 682-686 (2003).
Margulies et al., "Genome Sequencing in Microfabricated High-Density Picolitre Reactors," *Nature*, vol. 437, pp. 376-380 (2005); corrigendum at vol. 441, p. 120 (2006).
Matsumura et al., "Photochemical Transition of 5-Methylcytosine to Thymine by DNA Photoligation," *Nucleic Acids Symposium Series*, No. 51, pp. 233-234 (2007).
Ronaghi et al., "Real-Time DNA Sequencing Using Detection of Pyrophosphate Release," *Analytical Biochemistry*, vol. 242, pp. 84-89 (1996).
Roth et al., "Characterization of Broken DNA Molecules Associated With V(D)J Recombination," *Proc. Natl. Acad. Sci. USA*, vol. 90, pp. 10788-10792 (1993).
Ruparel et al., "Design and Synthesis of a 3-O-Allyl Photocleavable Fluorescent Nucleotide as a Reversible Terminator for DNA Sequencing by Synthesis," *Proc. Natl. Acad. Sci. USA*, 102: 5932-5937 (2005).
Smith et al., "Rapid Whole-Genome Mutational Profiling Using Next-Generation Sequencing Technologies," *Genome Research*, vol. 18, pp. 1638-1642 (2009).
Zilberman et al., "Genome-Wide Analysis of DNA Methylation Patterns," *Development*, vol. 134, pp. 3959-3965 (2007).
International Search Report and Written Opinion dated Feb. 25, 2010, for counterpart International Application No. PCT/CN2009/074851.
Office Action dated Mar. 26, 2012, for U.S. Appl. No. 12/613,291.
Reply to Office Action dated Jun. 1, 2012, for U.S. Appl. No. 12/613,291.
Office Action dated Nov. 5, 2012, for U.S. Appl. No. 12/613,291.
Reply to Office Action dated Jan. 30, 2013, for U.S. Appl. No. 12/613,291.
Final Office Action dated Apr. 5, 2013, for U.S. Appl. No. 12/613,291.
Reply to Final Office Action dated May 6, 2013, for U.S. Appl. No. 12/613,291.
Pacific Biosciences, "Harnessing Nature's Powerful Sequencing Engine: Single-Molecule Real-Time DNA Sequencing," slides 1-12 and 27-36, labeled Cold Spring Harbor Personal Genomes Meeting, Oct. 12, 2008.
Author Unknown, Cold Spring Harbor Personal Genomes Meeting Program, pp. 1-4, Oct. 2008.
Office Action dated Apr. 8, 2013, for U.S. Appl. No. 13/492,593.
Response to Restriction Requirement dated May 6, 2013, for U.S. Appl. No. 13/492,593.
Extended European Search Report and Preliminary Opinion issued by the European Patent Office in European Patent Application No. 09824428.8, dated May 24, 2013.
Notice of Reasons for Refusal in Japanese Patent Application No. JP 2011-534995, dated Jun. 11, 2013, and English translation thereof.
Office Action dated Jul. 15, 2013, for U.S. Appl. No. 13/492,593.
Reply to Office Action dated Aug. 22, 2013, for U.S. Appl. No. 13/492,593.
Notice of Allowance and Fee(s) Due dated Nov. 4, 2013, for U.S. Appl. No. 13/492,593.
Declaration—Bd.R. 203(b) in Patent Interference No. 105,970, dated Oct. 29, 2013, Administrative Patent Judge Deborah Katz.
Office Action dated Oct. 4, 2018, for U.S. Appl. No. 15/659,585.
Amendment dated Jan. 3, 2019, for U.S. Appl. No. 15/659,585.
Final Office Action dated Apr. 25, 2019, for U.S. Appl. No. 15/659,585.
Amendment and Response to Office Action dated Jul. 2, 2019, for U.S. Appl. No. 15/659,585.
Notice of Allowance and Fee(s) Due dated Aug. 2, 2019, for U.S. Appl. No. 15/659,585.

* cited by examiner

Reading result from a circular template

METHODS FOR ACCURATE SEQUENCE DATA AND MODIFIED BASE POSITION DETERMINATION

This is a divisional of U.S. patent application Ser. No. 14/286,904, filed May 23, 2014, which is a divisional of U.S. patent application Ser. No. 13/889,298, filed May 7, 2013, which is a divisional of U.S. patent application Ser. No. 13/492,593, filed Jun. 8, 2012, which is a divisional of U.S. patent application Ser. No. 12/613,291, filed Nov. 5, 2009, now U.S. Pat. No. 8,486,630, and claims the benefit of U.S. Provisional Patent Application No. 61/112,548, filed on Nov. 7, 2008, and of U.S. Provisional Patent Application No. 61/167,313, filed on Apr. 7, 2009, all of which are incorporated herein by reference.

The present invention relates to methods of determining the sequence of nucleic acids and of identifying the positions of modified bases in nucleic acids.

BACKGROUND OF THE INVENTION

Recent developments in DNA sequencing technology have raised the possibility of highly personalized, preventive medicine on the genomic level. Additionally, the possibility of rapidly acquiring large amounts of sequence data from multiple individuals within one or more populations may usher in a new phase of the genomics revolution in biomedical science.

Single base differences between genotypes can have substantial phenotypic effects. For example, over 300 mutations have been identified in the gene encoding phenylalanine hydroxylase (PAH), the enzyme that convertsphenylalanine to tyrosine in phenylalanine catabolism and protein and neurotransmitter biosynthesis that result in a deficient enzyme activity and lead to the disorders hyperphenylalaninaemia and phenylketonuria. See, e.g., Jennings et al., *Eur J Hum Genet* 8, 683-696 (2000).

Sequence data can be obtained using the Sanger sequencing method, in which labeled dideoxy chain terminator nucleotide analogs are incorporated in a bulk primer extension reaction and products of differing lengths are resolved and analyzed to determine the identity of the incorporated terminator. See, e.g., Sanger et al., *Proc Natl Acad Sci USA* 74, 5463-5467 (1997). Indeed, many genome sequences have been determined using this technology. However, the cost and speed of acquiring sequence data by Sanger sequencing can be limiting.

New sequencing technologies can produce sequence data at an astounding rate—hundreds of megabases per day, with costs per base lower than for Sanger sequencing. See, e.g., Kato, *Int J Clin Exp Med* 2, 193-202 (2009), However, the raw data obtained using these sequencing technologies can be more error prone than traditional Sanger sequencing. This can result from obtaining information from individual DNA molecules instead of a bulk population.

For example, in single molecule sequencing by synthesis, a base could be skipped due to the device missing a weak signal, or due to lack of signal resulting from fluorescent dye bleaching, or due to the polymerase acting too fast to be detected by device. All of the above events result in a deletion error in the raw sequence. Similarly, mutation errors and insertion errors can also happen at a higher frequency for the simple reasons of potentially weaker signals and faster reactions than in conventional methods.

Low accuracy sequence data is more difficult to assemble. In large scale sequencing, such as sequencing a complete eukaryotic genome, the DNA molecules are fragmented into smaller pieces. These pieces are sequenced in parallel, and then the resultant reads are assembled to reconstruct the whole sequence of the original sample DNA molecules. The fragmentation can be achieved, for example, by mechanical shearing or enzymatic cleavage.

Assembly of small reads of sequence into a large genome requires that the fragmented reads are accurate enough to be correctly grouped together. This is generally true for the raw sequencing data generated from the Sanger method, which can have a raw data accuracy of higher than 95%. Accurate single molecular sequencing technology could be applied to detect single-base modifications or mutations nucleic acid samples. However, the raw data accuracy for single molecule sequencing technologies may be lower due to the limitations discussed above. The accuracy of individual reads of raw sequence data could be as low as 60 to 80%. See, e.g.; Harris et al., Science 320:106-109 (2008). Thus, it would be useful to provide accurate single molecule sequencing methods.

Additionally, DNA methylation plays a critical role in the regulation of gene expression; for example, methylation at promoters often leads to transcriptional silencing. Methylation is also known to be an essential mechanism in genomic imprinting and X-chromosome inactivation. However, progress in deciphering complex whole genome methylation profiles has been limited. Therefore, methods of determining DNA methylation profiles in a high-throughput manner could be useful, more so should the methods also provide for accurate determination of sequence.

SUMMARY OF THE INVENTION

In some embodiments, the invention provides a method of determining the sequence of a nucleic acid sample comprising (a) providing a circular nucleic acid molecule comprising at least one insert-sample unit comprising a nucleic acid insert and the nucleic acid sample, wherein the insert has a known sequence; (b) obtaining sequence data comprising sequence of at least two insert-sample units, wherein a nucleic acid molecule is produced that comprises at least two insert-sample units; (c) calculating scores of the sequences of at least two inserts of the sequence data of step (b) by comparing the sequences to the known sequence of the insert; (d) accepting or rejecting at least two of the repeats of the sequence of the nucleic acid sample of the sequence data of step (b) according to the scores of one or both of the sequences of the inserts immediately upstream and downstream of the repeat of the sequence of the nucleic acid sample; (e) compiling an accepted sequence set comprising at least one repeat of the sequence of the nucleic acid sample accepted in step d; and (f) determining the sequence of the nucleic acid sample using the accepted sequence set.

In some embodiments, the invention provides a system comprising a sequencing apparatus operably linked to a computing apparatus comprising a processor, storage, bus system, and at least one user interface element, the storage being encoded with programming comprising an operating system, user interface software, and instructions that, when executed by the processor, optionally with user input, perform a method comprising: (a) obtaining sequence data from a circular nucleic acid molecule comprising at least one insert-sample unit comprising a nucleic acid insert and a nucleic acid sample, wherein: (i) the insert has a known sequence; (ii) the sequence data comprise sequence of at least two insert-sample units, and (iii) a nucleic acid molecule is produced that comprises at least two insert-sample units; (b) calculating scores of the sequences of at least two inserts of the sequence data of step (a) by comparing the sequences to the known sequence of the insert; (c) accepting or rejecting at least two of the repeats of the sequence of the nucleic acid sample of the sequence data of step (a) according to the scores of one or both of the sequences of the inserts immediately upstream and downstream of the repeat of the sequence of the nucleic acid sample; (d) compiling an accepted sequence set comprising at least one repeat of the sequence of the nucleic acid sample accepted in step (c); and (e) determining the sequence of the nucleic acid sample using the accepted sequence set, wherein an output of the system is used to produce at least one of (i) a sequence of a nucleic acid sample or (ii) an indication that there is a modified base in at least one position in a nucleic acid sample.

In some embodiments, the invention provides a storage encoded with programming comprising an operating system, user interface software, and instructions that, when executed by the processor on a system comprising a sequencing apparatus operably linked to a computing apparatus comprising a processor, storage, bus system, and at least one user interface element, optionally with user input, perform a method comprising: (a) obtaining sequence data from a circular nucleic acid molecule comprising at least one insert-sample unit comprising a nucleic acid insert and a nucleic acid sample, wherein: (i) the insert has a known sequence, (ii) the sequence data comprise sequence of at least two insert-sample units, and (iii) a nucleic acid molecule is produced that comprises at least two insert-sample units; (b) calculating scores of the sequences of at least two inserts of the sequence data of step (a) by comparing the sequences to the known sequence of the insert; (c) accepting or rejecting at least two of the repeats of the sequence of the nucleic acid sample of the sequence data of step (a) according to the scores of one or both of the sequences of the inserts immediately upstream and downstream of the repeat of the sequence of the nucleic acid sample; (d) compiling an accepted sequence set comprising at least one repeat of the sequence of the nucleic acid sample accepted in step (c); and (e) determining the sequence of the nucleic acid sample using the accepted sequence set, wherein the method results in output used to produce at least one of (i) a sequence of a nucleic acid sample or (ii) an indication that there is a modified base in at least one position in a nucleic acid sample.

In some embodiments, the invention provides a method of determining a sequence of a double-stranded nucleic acid sample and a position of at least one modified base in the sequence, comprising: (a) locking the forward and reverse strands together to form a circular pair-locked molecule; (b) obtaining sequence data of the circular pair-locked molecule via single molecule sequencing, wherein the sequence data comprises sequences of the forward and reverse strands of the circular pair-locked molecule; (c) determining the sequence of the double-stranded nucleic acid sample by comparing the sequences of the forward and reverse strands of the circular pair-locked molecule; (d) altering the base-pairing specificity of bases of a specific type in the circular pair-locked molecule to produce an altered circular pair-locked molecule; (e) obtaining the sequence data of the altered circular pair-locked molecule wherein the sequence data comprises sequences of the altered forward and reverse strands; and (f) determining the positions of modified bases in the sequence of the double-stranded nucleic acid sample by comparing the sequences of the altered forward and reverse strands.

In some embodiments, the invention provides a method of determining a sequence of a double-stranded nucleic acid sample, comprising: (a) locking the forward and reverse strands of the nucleic acid sample together to form a circular pair-locked molecule; (b) obtaining sequence data of the circular pair-locked molecule via single molecule sequencing, wherein sequence data comprises sequences of the forward and reverse strands of the circular pair-locked molecule; and (c) determining the sequence of the double-stranded nucleic acid sample by comparing the sequences of the forward and reverse strands of the circular pair-locked molecule.

In some embodiments, the invention provides a method of determining a sequence of a double-stranded nucleic acid sample and a position of at least one modified base in the sequence, comprising: (a) locking the forward and reverse strands of the nucleic acid sample together to form a circular pair-locked molecule; (b) obtaining sequence data of the circular pair-locked molecule via single molecule sequencing, wherein sequence data comprises sequences of the forward and reverse strands of the circular pair-locked molecule; and (c) determining the sequence of the double stranded nucleic acid sample and the position of the at least one modified base in the sequence of the double stranded nucleic acid sample by comparing the sequences of the forward and reverse strands of the circular pair-locked molecule.

In some embodiments, the invention provides a method of determining a sequence of a double-stranded nucleic acid sample and a position of at least one modified base in the sequence, comprising: (a) locking the forward and reverse strands of the nucleic acid sample together to form a circular pair-locked molecule; (b) altering the base-pairing specificity of bases of a specific type in the circular pair-locked molecule; (c) obtaining sequence data of the circular pair-locked molecule via single molecule sequencing, wherein sequence data comprises sequences of the forward and reverse strands of the circular pair-locked molecule; and (d) determining the sequence of the double-stranded nucleic acid sample and the position of the at least one modified base in the sequence of the double-stranded nucleic acid sample by comparing the sequences of the forward and reverse strands of the circular pair-locked molecule.

In some embodiments, the invention provides a method of determining a sequence of a double-stranded nucleic acid sample and a position of at least one modified base in the sequence, comprising: (a) locking the forward and reverse strands together to form a circular pair-locked molecule; (b) obtaining sequence data of the circular pair-locked molecule via single molecule sequencing, wherein the sequence data comprises sequences of the forward and reverse strands of the circular pair-locked molecule; (c) determining the sequence of the double-stranded nucleic acid sample by comparing the sequences of the forward and reverse strands of the circular pair-locked molecule; (d) obtaining sequencing data of the circular pair-locked molecule via single molecule sequencing, wherein at least one nucleotide analog that discriminates between a base and its modified form is used to obtain sequence data comprising at least one position wherein the at least one differentially labeled nucleotide analog was incorporated; and (e) determining the positions of modified bases in the sequence of the double-stranded nucleic acid sample by comparing the sequences of the forward and reverse strands.

In some embodiments, the invention provides a method of determining a sequence of a double-stranded nucleic acid sample and a position of at least one modified base in the sequence, comprising: (a) locking the forward and reverse strands of the nucleic acid sample together to form a circular pair-locked molecule; (b) obtaining sequence data of the circular pair-locked molecule via single molecule sequencing, wherein at least one nucleotide analog that discriminates between a base and its modified form is used to obtain sequence data comprising at least one position wherein the at least one differentially labeled nucleotide analog was incorporated; and (c) determining the sequence of the double-stranded nucleic acid sample and the position of the at least one modified base in the sequence of the double-stranded nucleic acid sample by comparing the sequences of the forward and reverse strands of the circular pair-locked molecule.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The foregoing aspects and advantages of this invention may become apparent from the following detailed description with reference to the accompanying drawings in which.

Circular pair-locked molecule.

Nucleotide conversion.

Obtaining sequence data and a methylation profile from a circular pair-locked molecule.

Raw and processed sequence data acquired from a circular nucleic acid molecule template.

If the circular template comprises a single nucleic acid sample and a single nucleic acid insert, then both of 22 and 24, along with subsequent nucleic acid sample sequences 26, 30, and 32, are sequences of the same single nucleic acid sample; likewise, 23, 25, 27, 29, and 31 are sequences of the same single nucleic acid insert in this case. If the circular template comprises forward and reverse repeats of the sequence of the nucleic acid sample and two nucleic acid inserts having known sequences, which may be identical or non-identical, as in the case of a circular pair-locked molecule, then the nucleic acid sample sequences have alternating orientations and correspond to the two nucleic acid sample repeats in an alternating manner (e.g., 22 could be in forward orientation, meaning it is a sequence of the reverse repeat, and 24 could be in reverse orientation, meaning it is a sequence of the forward repeat, or vice versa). Likewise, the nucleic acid insert sequences 23, 25, etc., would also correspond to the two nucleic acid inserts, which may be identical or non-identical, of the circular template in an alternating manner.

Figure 7A:
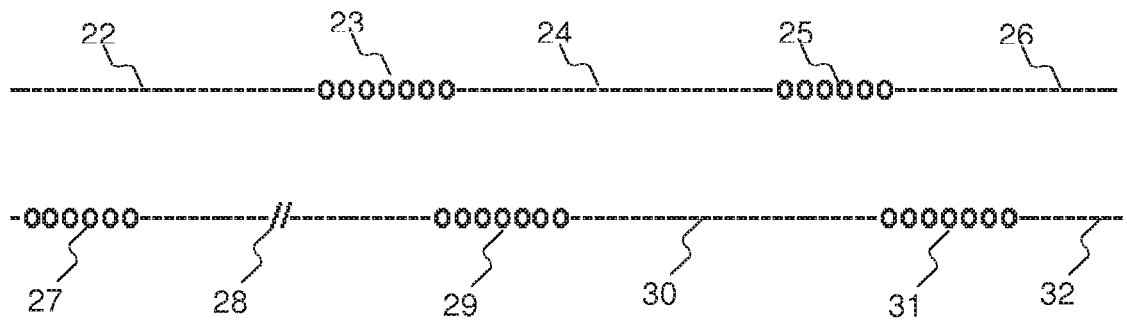
FIG. 7A. The content of sequence that can be obtained from a circular template is represented diagrammatically. Nucleic acid sample sequence is represented by dashes and nucleic acid insert sequence is represented by circles. The sequence illustrated begins with a partial sequence 22 of a nucleic acid sample, followed by the sequence of a nucleic acid insert 23; these are followed by a sequence 24 of the nucleic acid sample, a sequence 25 of a nucleic acid insert, a sequence 26 of the nucleic acid sample, and a sequence 27 of a nucleic acid insert. 28 represents additional sequence not shown in this figure, which is followed by a sequence 29 of a nucleic acid insert, a sequence 30 of the nucleic acid sample, a sequence 31 of a nucleic acid insert, and a partial sequence 32 of a nucleic acid sample.
Figure 7B:
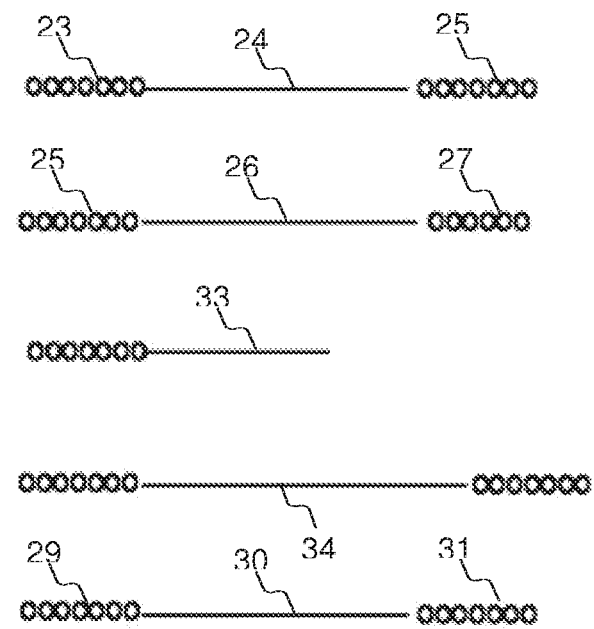

FIG. 7B. The sequence shown in FIG. 7A can be decomposed into segments each containing a repeat of the nucleic acid sample sequence, e.g., 24; the segments also comprise at least one repeat of the nucleic acid insert, for example, two repeats of the nucleic acid insert, e.g., 23 and 25. Some segments may contain only a partial sequence, e.g., 33, or an unusually long sequence, e.g., 34. Such segments can result from errors during sequencing. In some embodiments, such segments are excluded from further consideration.

Figure 8:
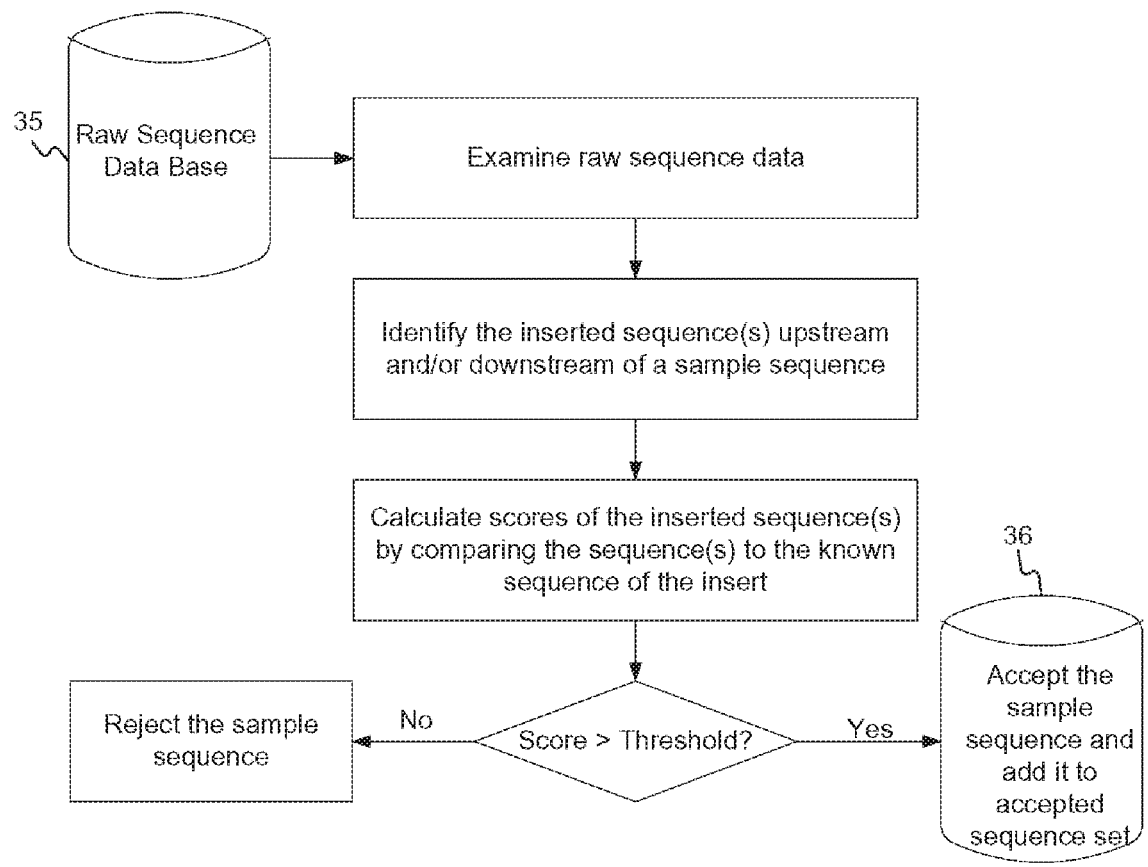

FIG. 8. Diagram of sequence processing steps. In some embodiments, raw sequence data are examined, processed, and accepted or rejected as shown. A raw sequence database 35 may be used. If a score is calculated that exceeds a threshold, a step 36 may be performed: accept the sample sequence and add it to an accepted sequence set.

Figure 9:
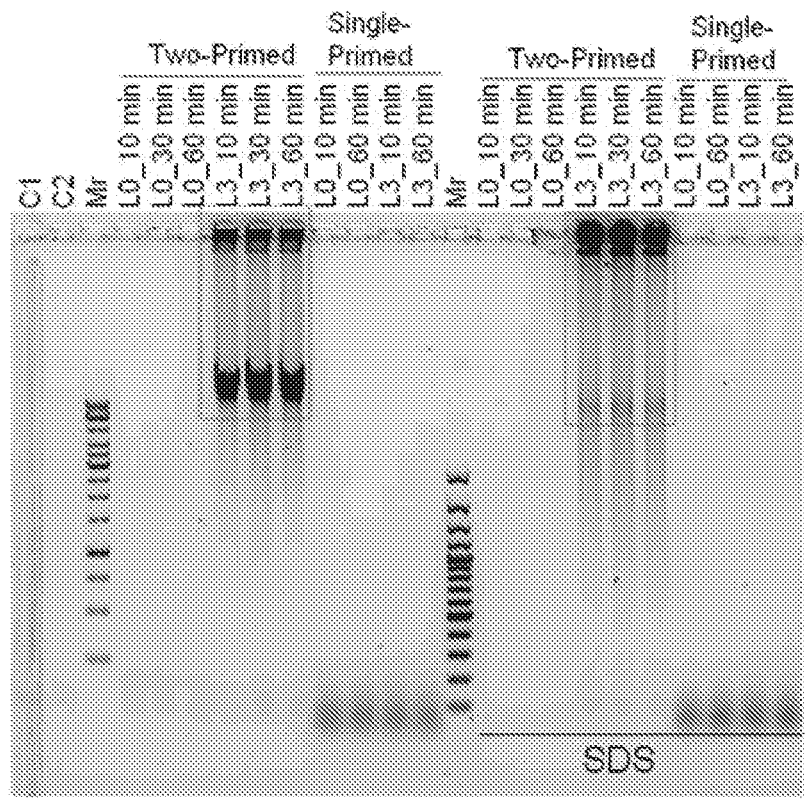

FIG. 9. Rolling circle amplification products. Products of the reactions described in Example 1 were electrophoresed and the gel was visualized as described, From the left, C1 and C2 are negative control lanes. The leftmost Mr lane contains the FERMENTAS GENERULER 1 kb ladder, Cat. No. SM0311, which band sizes ranging from 250 to 10,000 bp. The next ten lanes contain products of rolling circle amplification reactions as indicated, generated using two primers or one primer (amplification control) and products of the L0 (negative ligation control) or L3 reactions ligation reactions taken at the indicated times; see Example 1. The next Mr lane contains the FERMENTAS GENERULER 100 bp Plus ladder, Cat. No. SM0321, with band sizes ranging from 100 to 3,000 bp. The next ten lanes contain the same products as in the previous ten product lanes except that these products were mixed with loading dye containing 1% SDS.

Figures 10A, 10B:
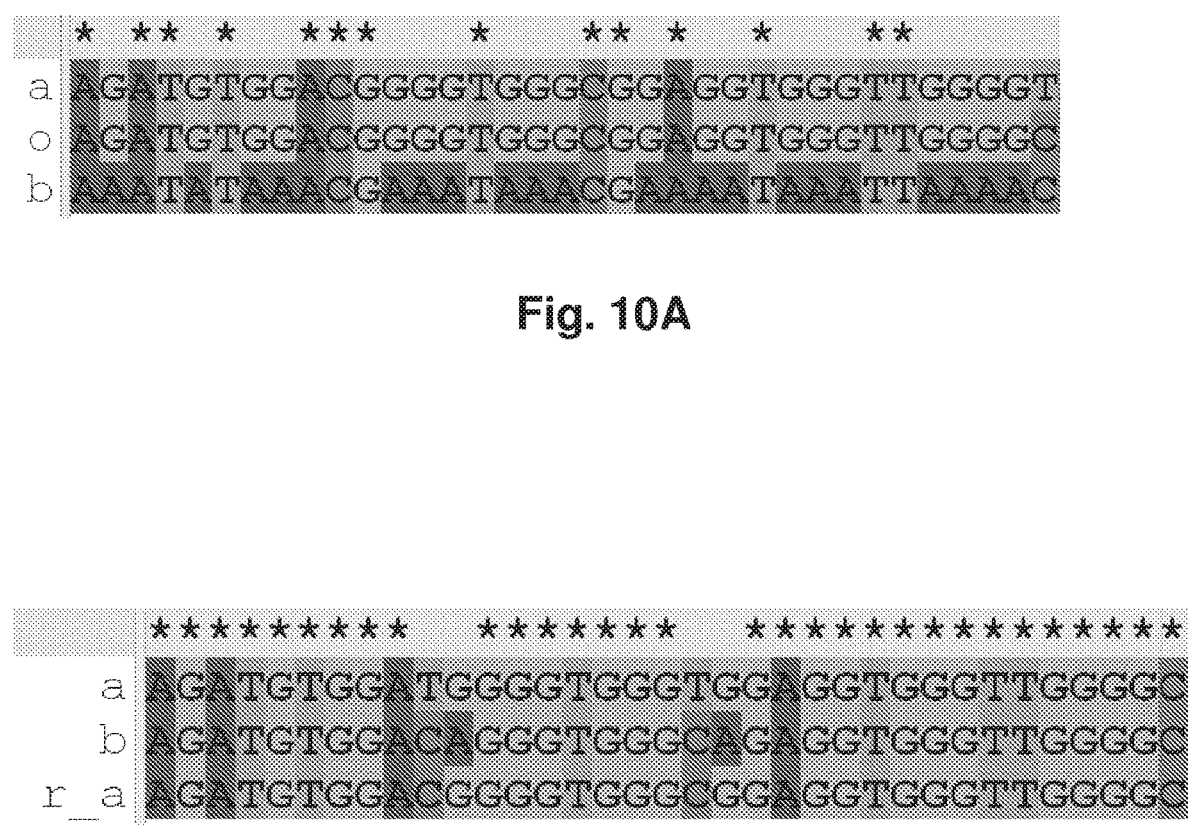

Alignments showing repeat sequences and deduced original sequence of a simulated nucleic acid sample. Positions where all aligned sequences agree are marked by asterisks. FIG. 10A. Reads a (residues 1 to 35 of SEQ ID NO: 10) and b (residues 1 to 35 of SEQ ID NO: 11) of Example 2 are shown together with the deduced original sequence, labeled 'o' (SEQ ID NO: 5), of the forward strand of the nucleic acid sample. The original sequence was deduced using the rules shown in Table 5. The positions where all three sequences shown have C are positions where the simulated nucleic acid sample contained a methylated cytosine in the forward strand. The positions where all three sequences shown have G are positions where the simulated nucleic acid sample contained a methylated cytosine in the reverse strand. FIG. 10B. Reads a (SEQ ID NO: 14) and b (SEQ ID NO: 15) of Example 3 are shown together with the deduced original sequence of the forward strand, marked 'r_a' (SEQ ID NO: 5), The original sequence was deduced using the rules in Table 6. The positions where the deduced original sequence has a C that disagrees with read a are positions where the simulated nucleic acid sample contained a methylated cytosine in the forward strand. The positions where the deduced original sequence has a G that disagrees with read b are positions where the simulated nucleic acid sample contained a methylated cytosine in the reverse strand.

Figure 11A:
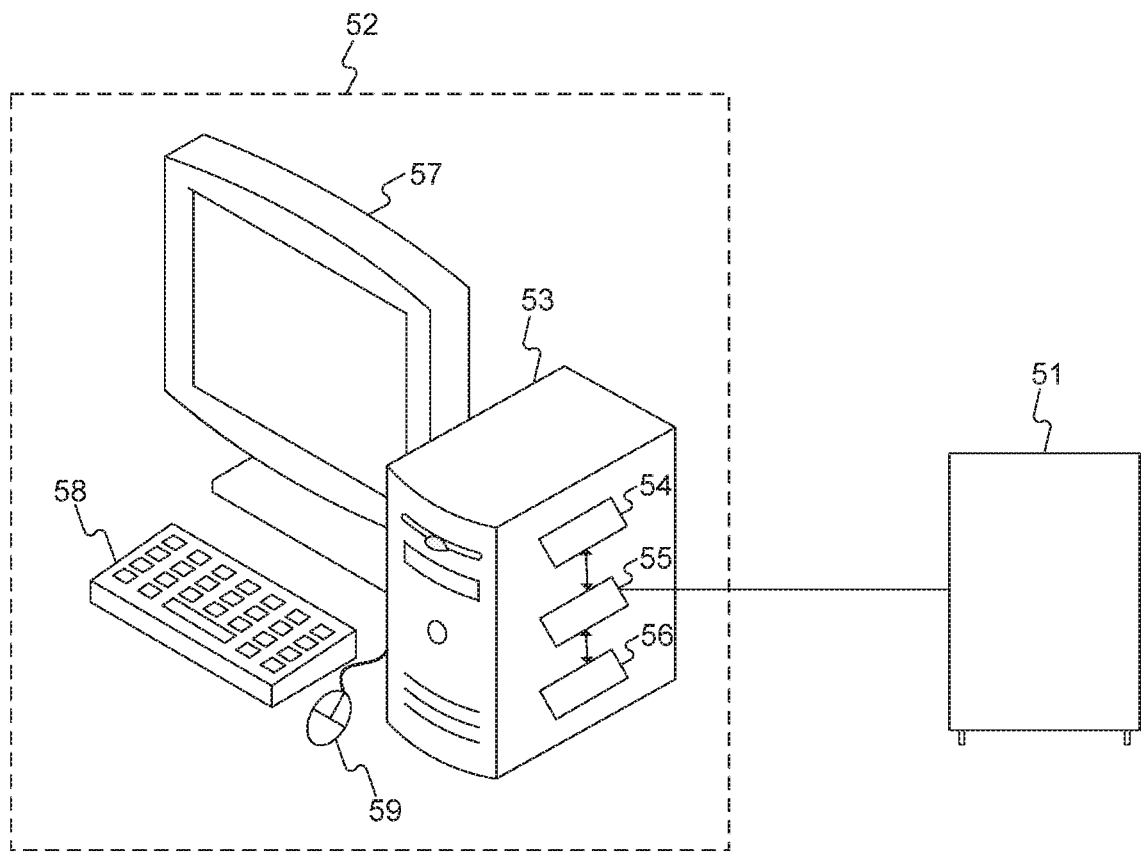
Figure 11B:
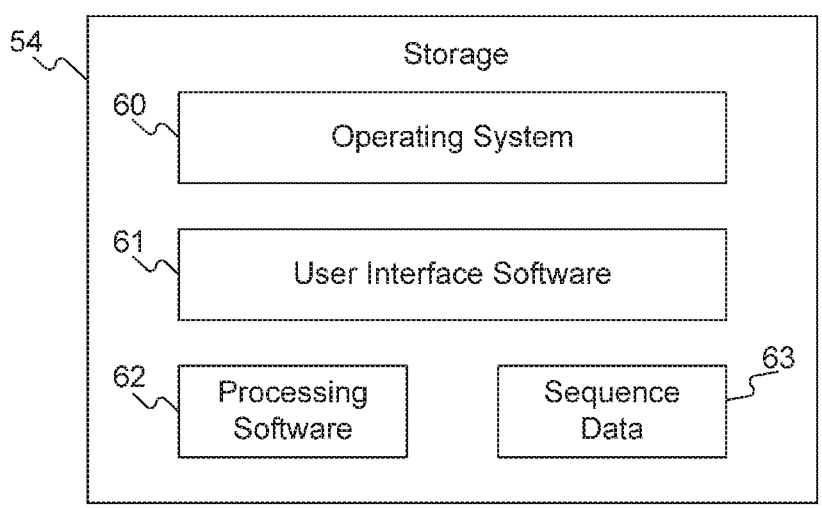

Computing apparatus and storage. FIG. 11A. In some embodiments, the invention relates to a sequencing apparatus 51 operably linked to a computing apparatus 52 comprising at least one user interface element chosen from a display 57, a keyboard 58, and a mouse 59, and at least one computer 53 comprising a storage 54 (see panel B), a bus system 55, and a processor 56. FIG. 11B, In some embodiments, the invention relates to a storage 54 comprising an operating system 60, user interface software 61 and processing software 62. The storage can additionally comprise sequence data 63 acquired from the sequencing apparatus (51 in FIG. 11A).

Figure 12:

FIG. 12, General scheme of sequence and 5-methylcytosine position determination of using bisulfite conversion with a linear pair locked molecule. A double stranded nucleic acid sample comprising 5-methylcytosine is provided (at top). A linear pair-locked molecule is constructed by ligating a hairpin insert to one double strand end of the molecule (beneath first arrow, at right), thereby locking the forward and reverse strands of the double-stranded sample together. Also, linear flaps are attached to the other double strand end (at left). Bisulfite conversion is performed, converting cytosines to uracils but leaving 5-methylcytosines unaffected. The molecule is copied by providing a primer that binds to the linear flap attached at the 3' end of the linear pair locked molecule and extending the primer with a polymerase. The ends can be processed, e.g., by restriction digestion, to prepare the molecule for subsequent cloning and/or sequencing.

Figure 13:
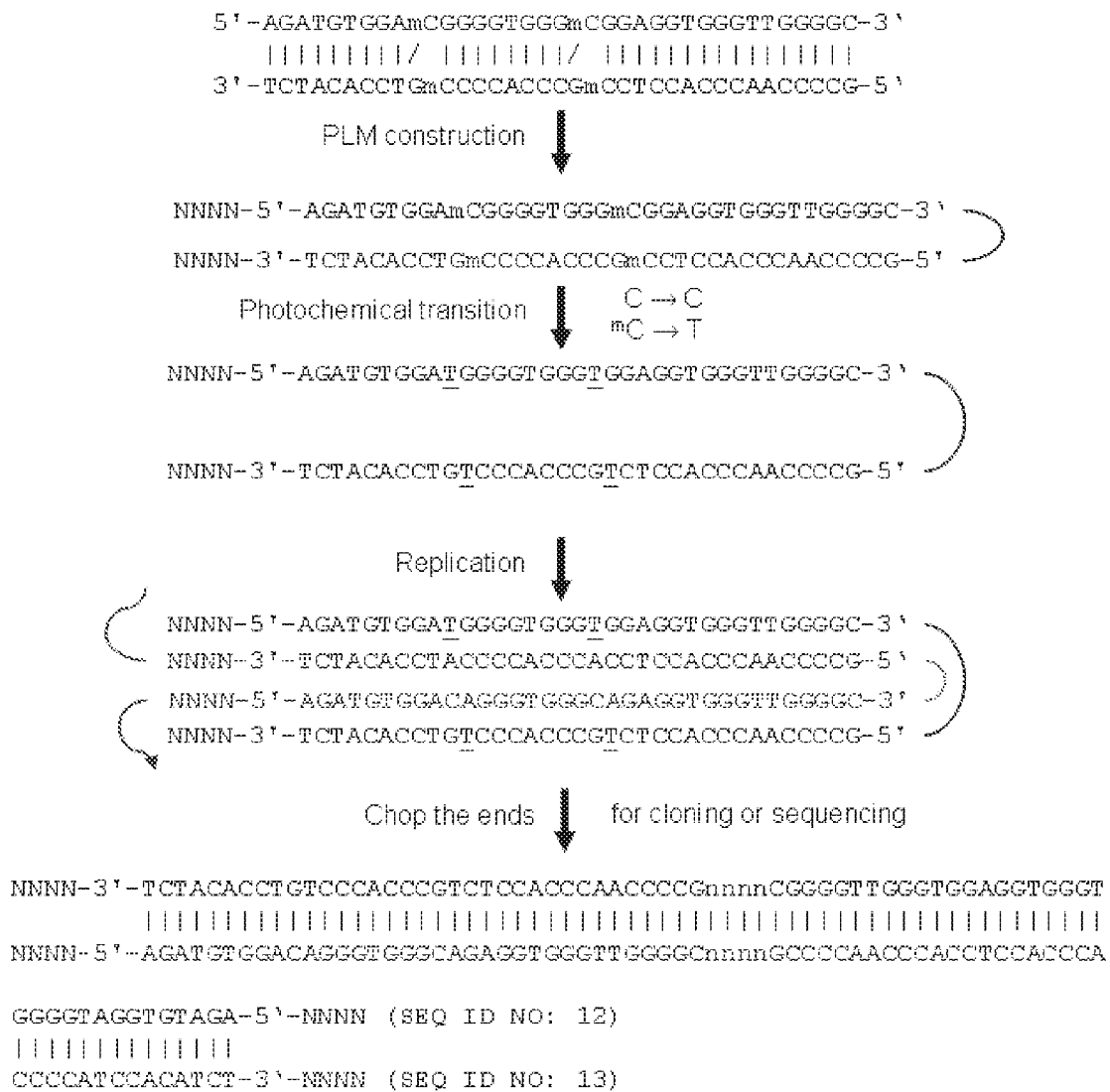

FIG. 13. General scheme of sequence and 5-methylcytosine position determination using photochemical transition with a linear pair locked molecule. A double stranded nucleic acid sample comprising 5-methylcytosine is provided (at top). A linear pair-locked molecule is constructed by ligating a hairpin insert to one double strand end of the molecule (beneath first arrow, at right), thereby locking the forward and reverse strands of the double-stranded sample together. Also, linear flaps are attached to the other double strand end (at left). Photochemical transition is performed, converting 5-methylcytosines to thymines but leaving unmodified cytosines unaffected. The molecule is copied by providing a primer that binds to the linear flap attached at the 3' end of the linear pair locked molecule and extending the primer with a polymerase. The ends can be processed, e.g., by restriction digestion, to prepare the molecule for subsequent cloning and/or sequencing.

Figure 14:
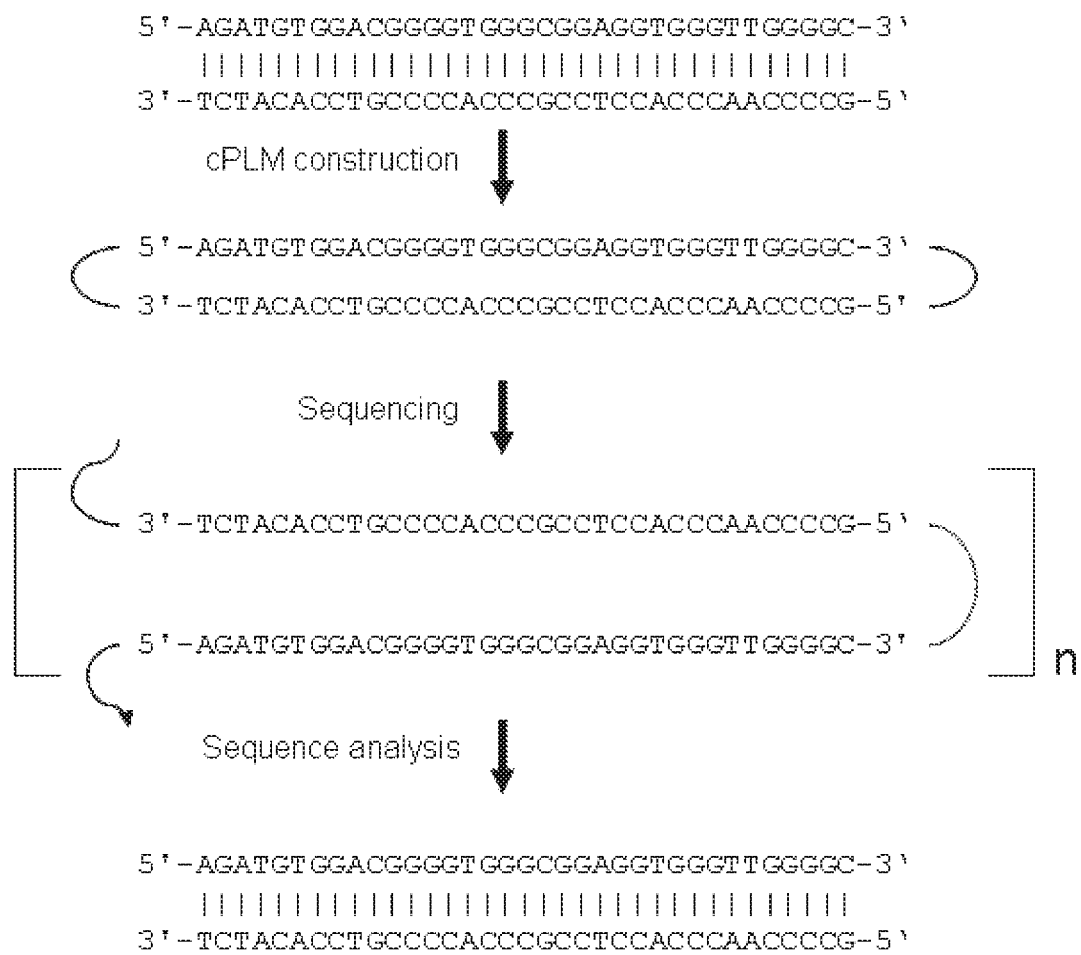

FIG. 14. General scheme of sequence determination using a circular pair locked molecule. A double stranded nucleic acid sample is provided (at top) (top strand: SEQ ID NO: 5; bottom strand: SEQ ID NO: 6). A circular pair-locked molecule is constructed by ligating a hairpin insert to both double strand ends of the molecule (beneath first arrow, at right and left), thereby locking the forward and reverse strands of the double-stranded sample together. Sequencing is performed, resulting in reads of SEQ ID NOs: 5 and 6, and the sequence data is analyzed to determine the sequence of the sample (SEQ ID NOs: 5 and 6); see, e.g., Example 5.

Figure 15:
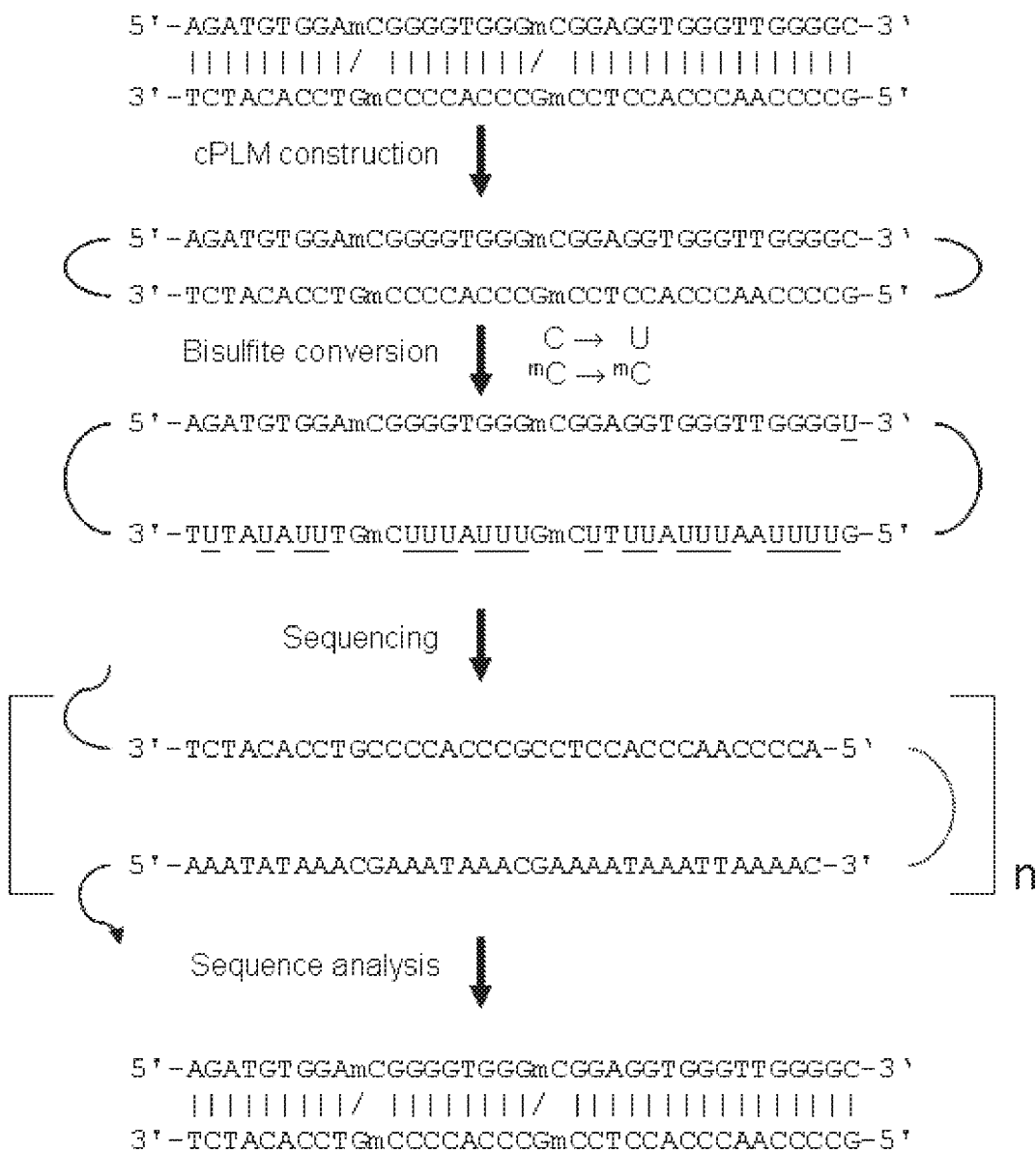

FIG. 15. General scheme of sequence and 5-methylcytosine position determination using bisulfite conversion and a circular pair locked molecule. A double stranded nucleic acid sample comprising 5-methylcytosine is provided (at top) (top strand: SEQ ID NO: 5; bottom strand: SEQ ID NO: 6). A circular pair-locked molecule is constructed by ligating a hairpin insert to both double strand ends of the molecule (beneath first arrow, at right and left), thereby locking the forward and reverse strands of the double-stranded sample together. Bisulfite conversion is performed, converting cytosines to uracils but leaving 5-methylcytosines unaffected. The product contains residues 1-35 and 40-74 of SEQ ID NO: 8. Sequencing is performed, resulting in reads of residues 1-35 and 40-74 of SEQ ID NO: 9, and the sequence data is analyzed to determine the sequence of the sample and 5-methylcytosine positions (SEQ ID NOs: 5 and 6); see, e.g., Example 6.

Figure 16:
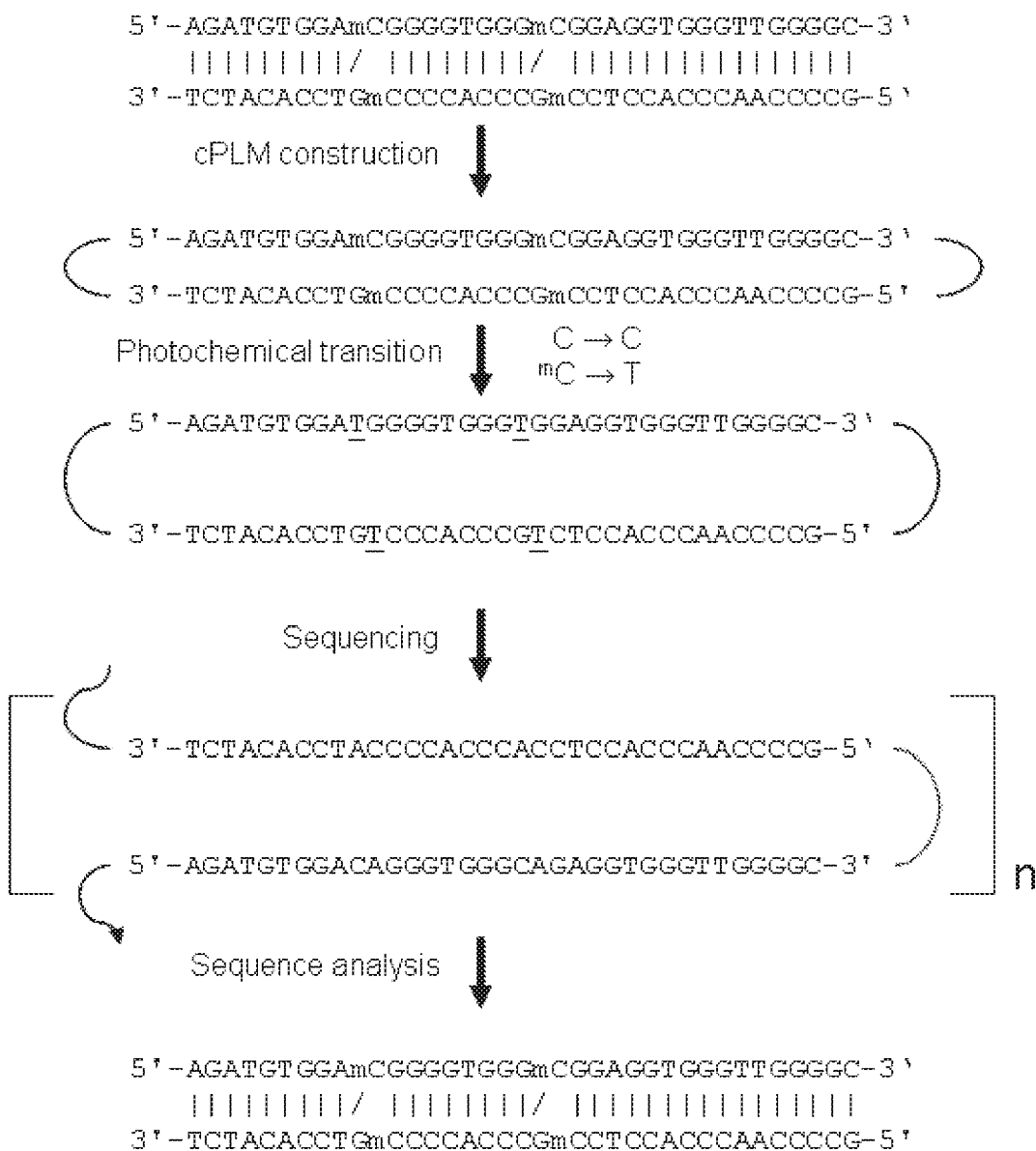

FIG. 16. General scheme of sequence and 5-methylcytosine position determination using photochemical transition and a circular pair locked molecule. A double stranded nucleic acid sample comprising 5-methylcytosine is provided (at top) (top strand: SEQ ID NO: 5; bottom strand: SEQ ID NO: 6). A circular pair-locked molecule is constructed by ligating a hairpin insert to both double strand ends of the molecule (beneath first arrow, at right and left), thereby locking the forward and reverse strands of the double-stranded sample together. Photochemical transition is performed, converting 5-methylcytosines to thymines but leaving unmodified cytosines unaffected. The product contains residues 1-35 and 40-74 of SEQ ID NO: 12. Sequencing is performed, resulting in reads of residues 1-35 and 40-74 of SEQ ID NO: 13, and the sequence data is analyzed to determine the sequence of the sample and 5-methylcytosine positions (SEQ ID NOs: 5 and 6); see, e.g., Example 7.

Figure 17:
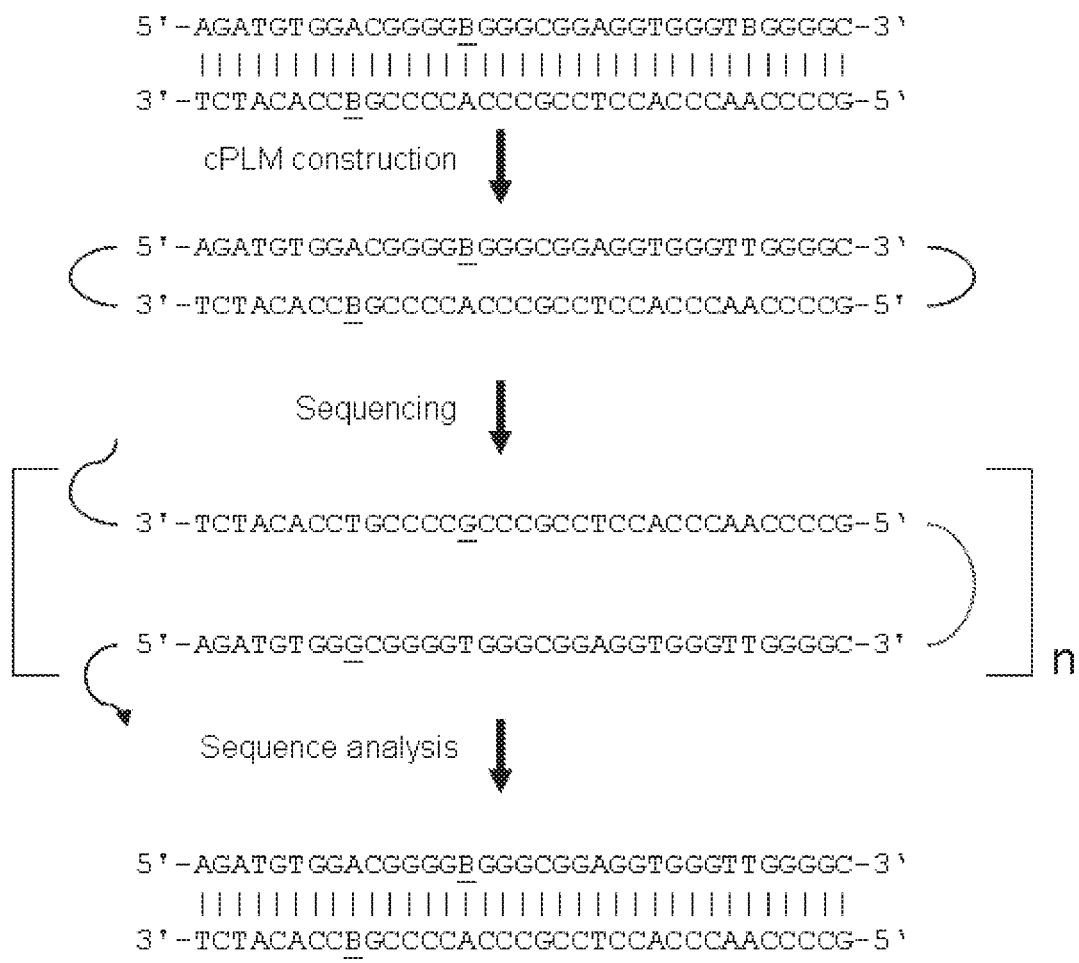

FIG. 17. General scheme of sequence and 5-bromouracil position determination using a circular pair locked molecule. A double stranded nucleic acid sample comprising 5-bromouracil is provided (at top) (top strand: SEQ ID NO: 16; bottom strand: SEQ ID NO: 17). A circular pair-locked molecule is constructed by ligating a hairpin insert to both double strand ends of the molecule (beneath first arrow, at right and left), thereby locking the forward and reverse strands of the double-stranded sample together. Sequencing is performed (resulting in reads of SEQ ID NOs: 18 and 19) and the sequence data is analyzed to determine the sequence of the sample and 5-bromouracil positions (SEQ ID NOs: 16 and 17); see, e.g., Example 8.

DETAILED DESCRIPTION OF THE INVENTION

Definitions

To facilitate the understanding of this invention, a number of terms are defined below. Terms not defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term nucleic acid includes oligonucleotides and polynucleotides.

High stringency conditions for hybridization refer to conditions under which two nucleic acids must possess a high degree of homology to each other to hybridize. Examples of high stringency conditions for hybridization include hybridization in 4× sodium chloride/sodium citrate (SSC), at 65 or 70° C., or hybridization in 4×SSC plus 50% formamide at about 42 or 50° C., followed by at least one, at least two, or at least three washes in 1×SSC, at 65 or 70° C.

Melting temperature refers to the temperature at which half of a nucleic acid in solution exists in a melted state and half exists in an unmelted state, assuming the presence of sufficient complementary nucleic acid. In the case of an oligonucleotide present in excess over complementary sequence, melting temperature is the temperature at which half of the complementary sequence is annealed with the oligonucleotide. In the case of a nucleic acid insert capable of forming a hairpin, melting temperature is the temperature at which half of the insert is in a partially self-hybridized "hairpin" form. As melting temperature is condition dependent, melting temperatures of oligonucleotides discussed herein refer to the melting temperature in an aqueous solution of 50 mM sodium chloride, with the oligonucleotide at 0.5 µM. Melting temperatures can be estimated by various methods known in the art, for example, using the nearest-neighbor thermodynamic parameters found in Allawi et al., *Biochemistry*, 36, 10581-10594 (1997) together with standard thermodynamic equations.

A site in a nucleic acid molecule is suitable for primer binding if it has a unique sequence in the nucleic acid molecule and is of a length and composition such that the complementary oligonucleotide has an acceptable melting temperature, for example, a melting temperature ranging from 45° C. to 70° C., from 50° C. to 70° C., from 45° C. to 65° C., from 50° C. to 65° C., from 55° C. to 70° C., from 60° C. to 70° C., from 55° C. to 60° C., from 60° C. to 65° C., or from 50° C. to 55° C.

Extending a primer, oligonucleotide, or nucleic acid refers to adding at least one nucleotide to the primer, oligonucleotide, or nucleic acid. This includes reactions catalyzed by polymerase or ligase activity.

A sequencing primer is an oligonucleotide that can bind to a site in a nucleic acid molecule that is suitable for primer binding and be extended in a sequencing reaction so as to produce sequence data.

A nucleic acid insert is capable of forming a hairpin if it can partially self-hybridize, and the self-hybridized form has a melting temperature of at least 15° C.

An overhang is a single stranded segment at the end of a double stranded nucleic acid molecule or hairpin.

A repeat or repeat sequence is a sequence that occurs more than once in a nucleic acid. When repeats are present in a nucleic acid molecule, all instances of the sequence, including the first instance, are considered repeats. Repeats include sequences that are reverse complements of each other, such as occur in a circular pair-locked molecule. Repeats also include sequences that are not exactly identical but are derived from the same sequence, e.g., sequences that differ due to misincorporation events or other polymerase errors during synthesis, or sequences that were initially identical or perfect reverse complements but differ due to modification by a procedure such as photochemical transition or bisulfite treatment.

A nucleic acid insert and a nucleic acid sample are immediately upstream or downstream of one another if there are no other intervening repeats of the insert or sample between the insert and sample. In a single stranded molecule, upstream refers to the 5' direction and downstream refers to the 3' direction. In a double stranded molecule, the polarity can be determined arbitrarily or it can be determined according to the polarity of directional elements such as promoters, coding sequences, etc., if a majority of such elements is oriented in the same way. The polarity of a promoter is that the direction of an initiating RNA polymerase's synthesis is downstream. The polarity of a coding sequence is that the direction from start to stop codon is downstream.

Two repeats are in forward and reverse orientations relative to each other, and have opposite orientations, if they are reverse complements of each other or one or both are derivatives of the reverse complement of each other. Which repeat is considered forward can be arbitrary or can be determined according to polarity of elements in the repeat, as discussed in the preceding paragraph.

A modified base is a base other than adenine, thymine, guanine, cytosine, or uracil that can be included in place of one or more of the aforementioned bases in a nucleic acid or nucleotide.

Ambiguity codes are codes that represent a combination of bases at a sequence, in the sense that any of the represented bases could be present, for example: Y=pyrimidine (C, U, or T); R=purine (A or G); W=weak (A, T, or U); S=strong (G or C); K=keto (T, U, or G); M=amino (C or A); D=not C (A, G, T, or U); V=not T or U (A, C, or G); H=not G (A, C, T, or U); B=not A (C, G, T, or U).

A position weight matrix is a matrix in which the rows correspond to positions in a nucleic acid sequence and the columns correspond to bases, or vice versa, and each element in the matrix is a weight for a particular base at a particular position. A sequence can be scored against a position weight matrix by summing the weights corresponding to each base of the sequence; for example, if the sequence is ACG, the score would be the sum of the weight for A in the first column of the matrix, the weight for C in the second column, and the weight for G in the third column, assuming columns corresponded to positions. A position weight matrix can be run over a sequence with a length greater than the number of positions in the matrix by iteratively scoring the sequence against the matrix, in which the starting position is incremented by one position in each run. In this way, a position in the sequence that produces a maximum or minimum score against the matrix can be identified.

Storage refers to a repository of digital information accessible by a computer. It includes RAM, ROM, hard drives, non-volatile solid state memory, optical disks, magnetic disks, and equivalents thereof.

A data structure is an object or variable in a storage that contains data. A data structure can contain scalar data (e.g., an individual character, number, or string), an assembly of scalar data (e.g., a matrix or array of scalars), or a recursive assembly (e.g., a list, which can be multidimensional, comprising sub-lists, matrices, arrays, and/or scalars as elements, with the sub-lists able themselves to contain sub-lists, matrices, arrays, and/or scalars as elements).

Nucleic Acid Sample

The methods of the invention comprise determining the sequence of a nucleic acid sample and/or determining the positions of modified bases in a nucleic acid sample. The term "nucleic acid sample" refers to the nucleic acid whose sequence and/or modified base positions are to be determined in the methods of the invention.

The nucleic acid sample can be obtained from a sources including, without limitation, DNA (including without limitation genomic DNA, cDNA, mtDNA, chloroplast DNA, and extrachromosomal or extracellular DNA) or RNA (including without limitation mRNA, primary transcript RNA, tRNA, rRNA, miRNA, siRNA, and snoRNA). The nucleic acid sample can be from an individual, patient, specimen, cell culture, biofilm, organ, tissue, cell, spore, animal, plant, fungus, protist, bacterium, archaeon, virus, or virion. In some embodiments, the nucleic acid sample is obtained as an environmental sample, e.g., from soil or a body of water; the nucleic acid sample may be obtained as an environmental sample without specific knowledge of whether the nucleic acid is of cellular, extracellular, or viral origin. In addition, the nucleic acid can be obtained from a chemical or enzymatic reaction, including reactions in which synthetic, recombinant, or naturally occurring nucleic acid is modified by an enzyme, for example, a methyltransferase.

In some embodiments, the nucleic acid sample is a processed sample from a source such as one of those listed above. For example, the isolated nucleic acid can be fragmented by shearing, such as by sonication or pipetting through a narrow aperture, or enzymatic digestion, such as with an endonuclease, which can be a restriction endonuclease. In some embodiments, the nucleic acid sample has at least one overhang. The isolated nucleic acid may first be cloned and propagated in a host cell and/or vector, e.g., as a bacterial or yeast artificial chromosome, a minichromosome, plasmid, cosmid, extrachromosomal element, or chromosomally integrated construct.

Providing a Circular Nucleic Acid Molecule

In some embodiments, the methods of the invention comprise providing a circular nucleic acid molecule comprising an insert-sample unit comprising a nucleic acid insert and the nucleic acid sample, wherein the insert has a known sequence. The circular nucleic acid molecule can be single or double stranded.

In some embodiments, the circular nucleic acid molecule is provided by isolating it in circular form from its source, if part of its sequence is known and thus can serve as the nucleic acid insert (e.g., a conserved motif within the sequence of a gene contained in the circular molecule may be known, or the molecule may be known to contain a sequence based on its ability to hybridize under high stringency conditions to another nucleic acid of known sequence). In some embodiments, the sequence of the nucleic acid insert is known only inexactly, as would be the case when knowledge of the sequence is derived from stringent hybridization properties. In some embodiments, the sequence of the nucleic acid insert is known exactly, such as would be the case when the circular nucleic acid molecule has a known backbone sequence or has been engineered to contain a known sequence.

In some embodiments, the circular nucleic acid molecule is provided by performing an in vitro reaction or reactions to incorporate the nucleic acid sample into the circular molecule along with a nucleic acid insert. The in vitro reaction or reactions can in some embodiments comprise ligation by a ligase and/or other strand joining reactions such as can be catalyzed by various enzymes, including recombinases and topoisomerases. DNA ligase or RNA ligase may be used to enzymatically join the two ends of a linear template, with or without an adapter molecule or linkers, to form a circle. For example, T4 RNA ligase couples single-stranded DNA or RNA, as described in Tessier et al., *Anal Biochem*, 158: 171-78 (1986). CIRCLIGASE™ (Epicentre, Madison, Wis.) may also be used to catalyze the ligation of a single stranded nucleic acid. Alternatively, a double stranded ligase, such as *E. coli* or T4 DNA ligase, may be used to perform the circularization reaction.

In some embodiments, providing the circular nucleic acid molecule comprises amplifying a nucleic acid template with primers (which may be random primers with 5' flaps of known sequence that can serve as the nucleic acid insert) comprising complementary regions and circularizing the amplified nucleic acid, such as may be catalyzed by a ligase or a recombinase; the amplified nucleic acid may in some embodiments be processed at its ends, e.g., by restriction or phosphorylation, prior to circularization.

In some embodiments, the circular nucleic acid molecule is provided by performing chemical circularization. Chemical methods employ known coupling agents such as BrCN plus imidazole and a divalent metal, N-cyanoimidazole with $ZnCl_2$, 1-(3-dimethylaminopropyl)-3 ethylcarbodiimide HCl, and other carbodiimides and carbonyl diimidazoles. The ends of a linear template may also be joined by condensing a 5'-phosphate and a 3'-hydroxyl, or a 5'-hydroxyl and a 3'-phosphate.

In some embodiments, the circular nucleic acid molecule is a circular pair-locked molecule (cPLM). This type of molecule is discussed in detail below.

Figure 1:
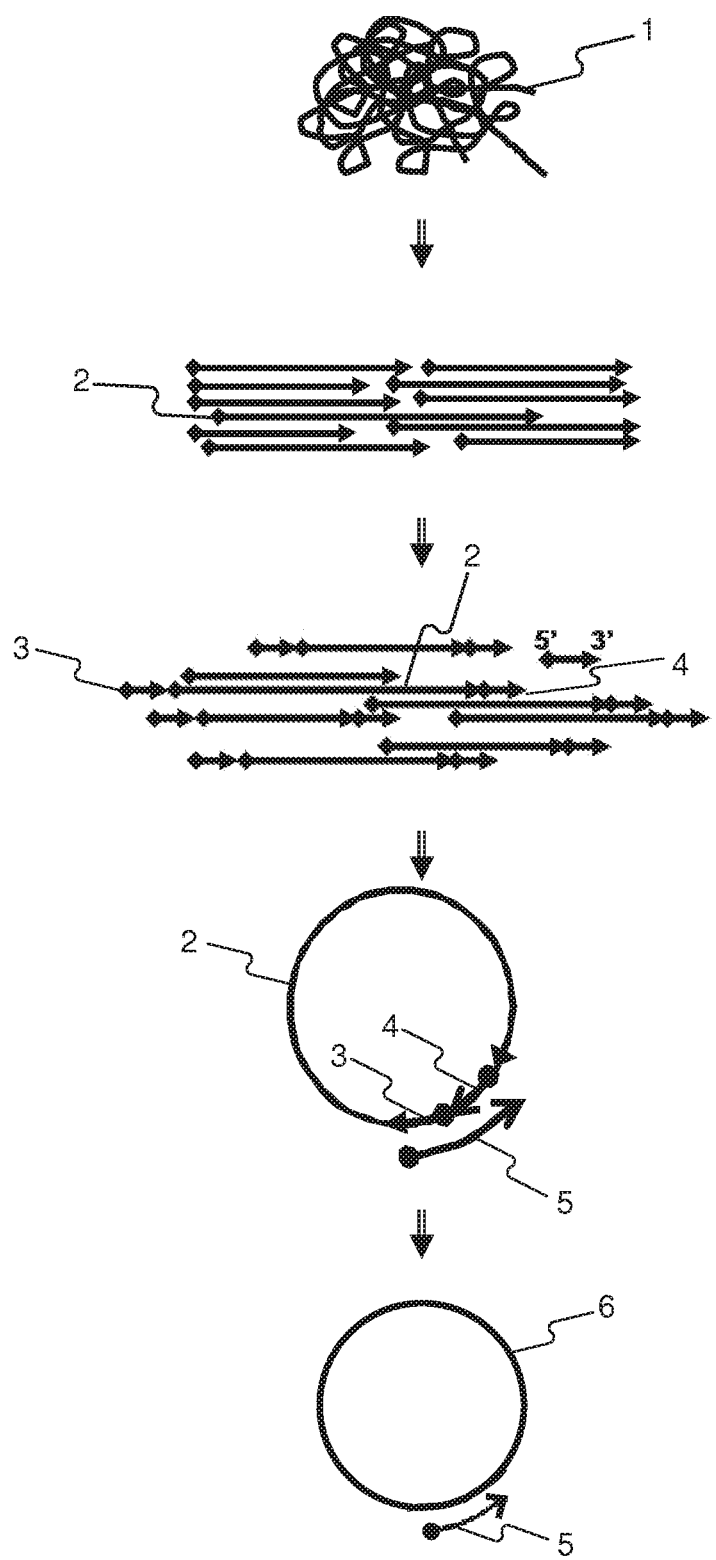
FIG. 1. Preparation of a circular DNA molecule in accordance with some embodiments of the invention. A DNA sample 1 is fragmented; a fragment 2 is ligated at its 5' end (diamond) to a linker 3 and at its 3' end (arrowhead) to another linker 4. The linkers 3 and 4 are complementary to adjoining segments of an oligonucleotide 5. Annealing of 5 to 3 and 4 provides a substrate for circularization by ligation, which reaction results in a circular molecule 6 comprising a nucleic acid insert (from the sequence of the linkers 3 and 4) and a nucleic acid sample (from the sequence of the fragment 2).
Figure 2:
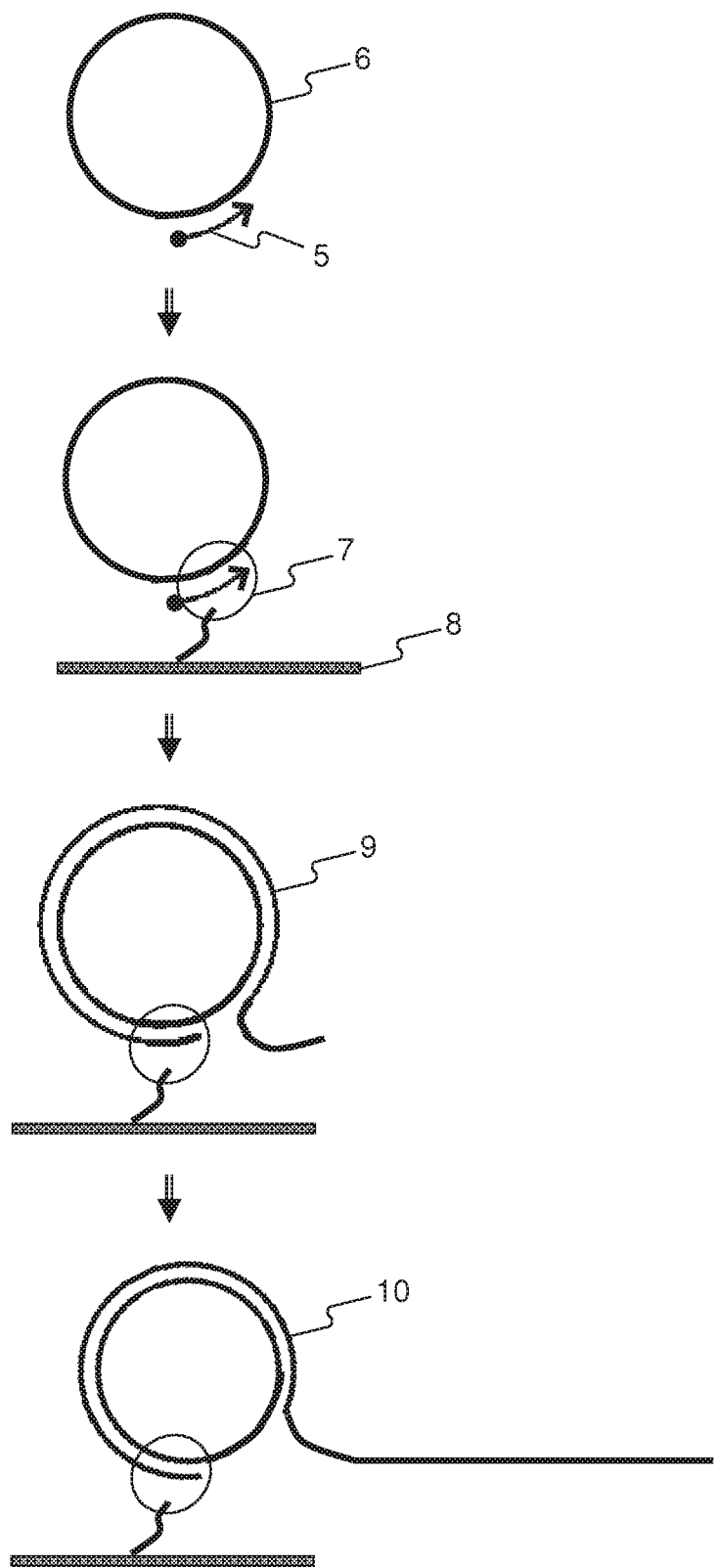
FIG. 2. Rolling circle amplification. An oligonucleotide 5, annealed to a circular molecule 6 produced as in FIG. 1, is bound by a polymerase 7 anchored to a surface 8. Extension of the oligonucleotide gives a complementary linear copy 9 of the circular molecule. Continued extension results in strand displacement and synthesis of a molecule 10 containing multiple copies of the circular molecule.
Figure 3A:
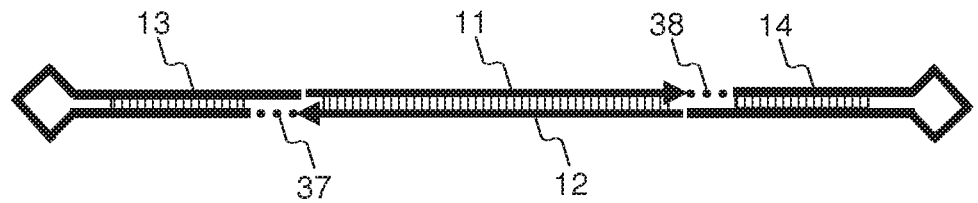
FIG. 3A. A double stranded molecule containing a forward strand 11 and reverse strand 12 can be combined with inserts that form hairpins 13 and 14, which may be identical or non-identical, to form a circular pair locked molecule. In some embodiments, the linkers have overhangs and recessed ends (37 and 38). These can be filled in using a polymerase or may be complementary to overhangs in the double stranded molecule (not shown). In a complete circular pair-locked molecule, 37 and 38 are filled in and sealed so that the molecule has a continuous, single stranded, and circular backbone.

Providing Forward and Reverse Repeats of the Nucleic Acid Sample; Circular Pair-Locked Molecules In some embodiments, the methods of the invention comprise providing forward and reverse repeats of a nucleic acid sample and locking the forward and reverse strands together to form a cPLM. The general structure of a cPLM is shown in FIG. 3A. A cPLM is a single-stranded circular nucleic acid molecule that comprises forward and reverse repeats of a nucleic acid sample; the repeats are bracketed by nucleic acid inserts, as shown in FIG. 3A. The nucleic acid inserts can be identical or non-identical. In some embodiments, the inserts have a length of at least 50 nt or at least 100 nt. In some embodiments, the inserts have a length ranging from 50 or 100 nt to 10,000 or 50,000 nt.

The strands of a linear double stranded nucleic acid sample can be locked together to form a cPLM, for example, by ligating nucleic acid inserts that form hairpins to each end of the molecule. In some embodiments, the nucleic acid inserts that form hairpins have melting temperatures of at least 20° C., 25° C., 30° C., 35° C., 40° C., 45° C., 50° C., 55° C., 60° C., 65° C., or 70° C. The ligation can be blunt-end or sticky-end ligation. Hairpin structures have base-paired stem regions and unpaired loop regions. In some embodiments, the insert nucleic acid comprises a loop region of a size of at least 20, 22, 25, 30, or 35 nucleotides. In some embodiments, this loop region is suitable for primer binding. In some embodiments, the loop region binds a primer with a melting temperature of at least 45° C., 50° C., 55° C., 60° C., 65° C., or 70° C.

In some embodiments, the nucleic acid sample comprises different sticky ends, such as could be generated by digestion using restriction enzymes with different restriction sites, and these different sticky ends favor ligation of different nucleic acid inserts. In some embodiments, the double stranded nucleic acid to be converted in this way can be obtained by extending a random primer comprising a 5' flap of known sequence along a template comprising the desired sample sequence.

The strands of a double stranded nucleic acid can also be locked together to form a cPLM by treatment with an enzyme that converts double-strand ends to hairpins, for example, recombinases that form a phosphotyrosine linkage with one strand of a double stranded molecule followed by hairpin formation through nucleophilic attack on the phosphotyrosine linkage by the other strand. Members of the family, such as λ integrase and Flp recombinase, are examples of such recombinases. See, e.g., Chen et al., *Cell* 69, 647-658 (1992); Roth et al., *Proc Natl Aced Sci USA* 90, 10788-10792 (1993). In some embodiments, the nucleic acid sample comprises recognition sequences for the enzyme that converts double-strand ends to hairpins. In some embodiments, recognition sequences for the enzyme that converts double-strand ends to hairpins are attached to the nucleic acid sample, e.g., by ligation.

In some embodiments, the sample nucleic acid is initially obtained in single stranded form and is converted to double stranded form prior to formation of a cPLM. This can be accomplished, for example, by ligating a hairpin with an overhang to the 3' end of the sample nucleic acid, and then extending from the 3' end of the ligated hairpin to synthesize a complementary strand. A second hairpin can then be joined to the molecule to form a cPLM.

Nucleic Acid Insert

The methods of the invention comprise providing and/or using circular nucleic acid molecules, including cPLMs, comprising at least one nucleic acid insert. In some embodiments, the at least one nucleic acid insert has a partially, inexactly, or completely known sequence, as discussed above. In some embodiments, the sequence of the at least one nucleic acid insert is completely known. In some embodiments, the at least one nucleic acid insert comprises a suitable binding site for an oligonucleotide, including a sequencing primer. In some embodiments, the at least one insert nucleic acid forms a hairpin.

In some embodiments, the at least one nucleic acid insert has a length ranging from 10 to 300, 15 to 250, 30 to 200, or 30 to 100 nucleotide residues. In some embodiments, the at least one nucleic acid insert has a melting temperature ranging from 45° C. to 70° C. or from 50° C. to 65° C.

In some embodiments, the at least one nucleic acid insert comprises a promoter, for example, the T7 RNA polymerase promoter. See, e.g., Guo et al., *J Biol Chem* 280, 14956-14961 (2005), A promoter is recognized by an RNA polymerase as a site for initiating RNA synthesis. Additional promoters are also known in the art.

Insert-Sample Unit

The circular nucleic acid molecules used in the methods of the invention comprise at least one nucleic acid sample and at least one nucleic acid insert grouped as at least one insert-sample unit. An insert-sample unit is a segment of nucleic acid in which a nucleic acid insert is immediately upstream or downstream of a nucleic acid sample.

Figure 3B:
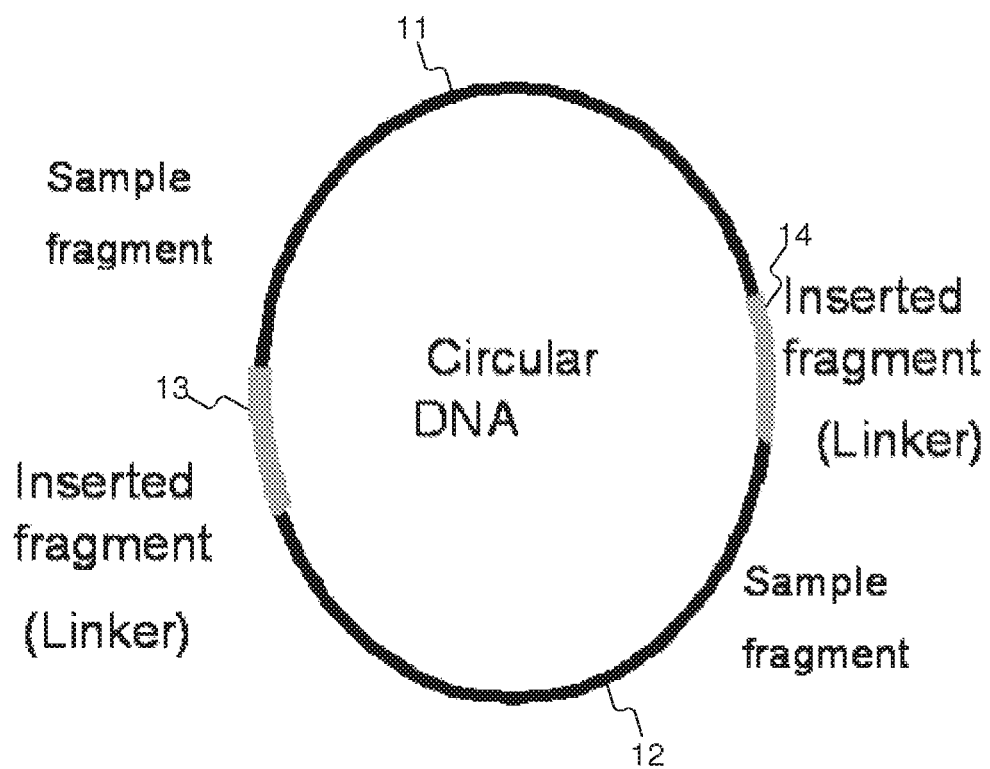
FIG. 3B. After gap filling and end joining as appropriate, a circular DNA is formed containing the forward strand 11, linker 14, reverse strand 12, and linker 13, shown here in melted form. The molecule can be converted to double stranded form, for example, by annealing a primer to one of the linkers and extending it using a polymerase without strand displacement activity, for example, E. coli DNA polymerase I, followed by ligation.
Figure 4:
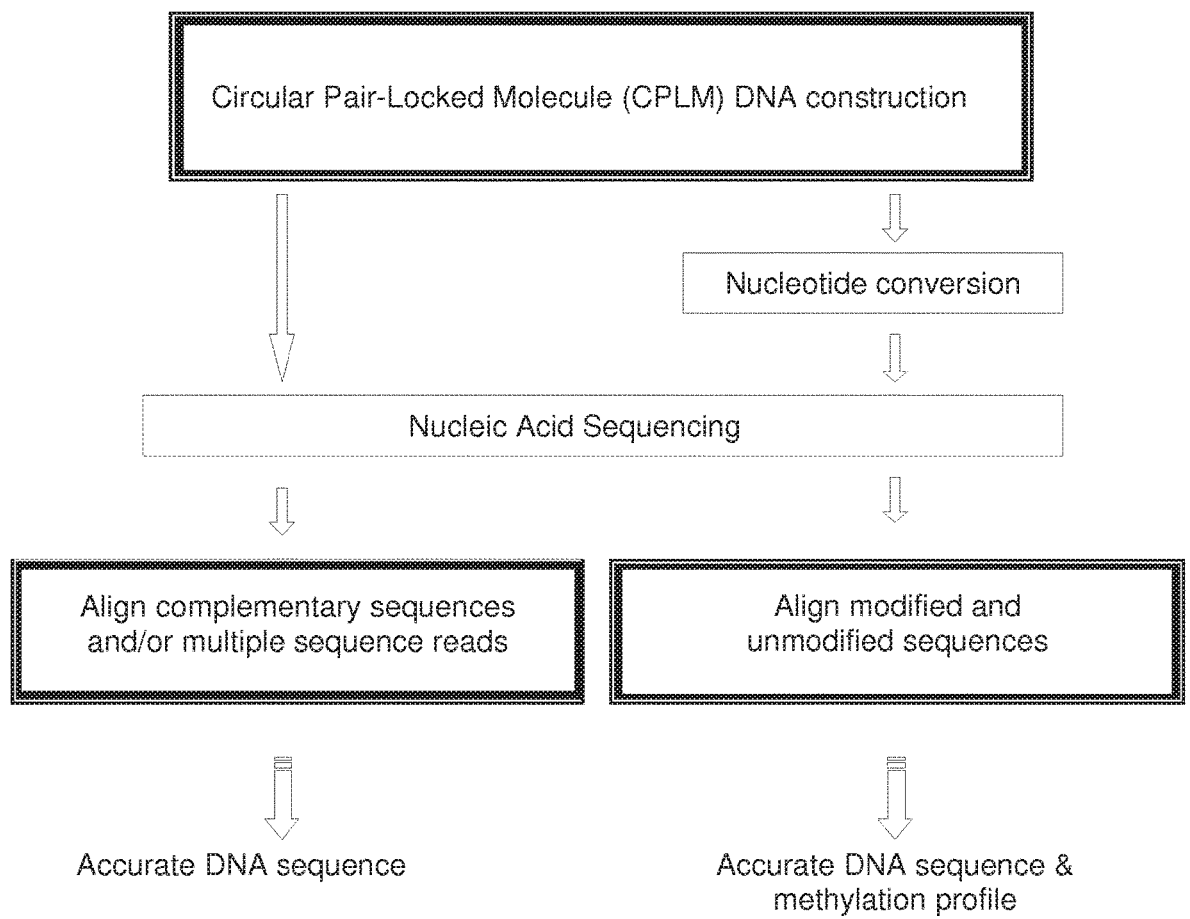
FIG. 4. Schemes for sequence determination and sequence and methylation profile determination using circular pair-locked molecules. (Left) A circular pair locked molecule can be sequenced for at least one full length of the molecule to provide complementary sequence reads; continued sequencing can be used to provide additional redundancy. The sequence data can be aligned and evaluated based on the sequences of the insert nucleic acids so as to obtain accurate sequence of the sample nucleic acid. (Right) Conversion of a specific type of nucleotide, such as by bisulfite conversion or photochemical transition, followed by sequencing, alignment; and comparison of the modified sequence and its unmodified complement can be used to obtain accurate sequence data and methylation profiles. Extended sequence reads containing multiple repeats of the sample nucleic acid sequence can be used for increased accuracy.

In some embodiments, the circular nucleic acid molecule is a cPLM, which comprises two insert-sample units; the nucleic acid samples in these two units are in opposite orientations to each other, that is, one is a forward repeat of the nucleic acid sample and the other is a reverse repeat. It should be noted that the cPLM may be considered to comprise two insert-sample units wherein the inserts are either upstream or downstream of the samples; that is, a cPLM conforming to the structure shown in FIG. 3B contains, in order, elements 11 (forward repeat), 14 (insert), 12

(reverse repeat), and 13 (insert), with 13 connecting back to 11 to close the circle. No matter whether the insert-sample units are considered to be 11 with 14, and 12 with 13, or 13 with 11, and 14 with 12, the molecule contains two insert-sample units. In embodiments in which the orientation of the insert and/or its positioning relative to the sample is functionally significant, e.g., the insert comprises a promoter or a primer binding site, it may be most efficient to group the insert-sample units so as to group the insert with the sample toward which the primer binding site or promoter is oriented, i.e., the sample which would be copied first by a polymerase initiating from the primer binding site or promoter.

Obtaining Sequence Data

Sequencing Method

The methods of the invention comprise obtaining sequence data. In some embodiments, a nucleic acid molecule is produced that comprises at least two insert sample units during the step of obtaining sequence data. In some embodiments, the nucleic acid molecule comprising at least two insert sample units an be produced by synthesizing it from the provided circular nucleic acid molecule. In some embodiments, the nucleic acid molecule comprising at least two insert sample units can be produced by altering the provided circular nucleic acid molecule, e.g., by converting the circular nucleic acid molecule to a linear nucleic acid molecule, which may be single-stranded in some embodiments. In some embodiments, at least one phosphodiester bond in a nucleic acid molecule, which may be the provided circular nucleic acid molecule or a template synthesis product thereof, is formed or broken in the step of obtaining sequence data.

In some embodiments, sequence data is obtained using a sequencing by synthesis method. In some embodiments, sequence data is obtained using a single molecule sequencing method. In some embodiments, the single molecule sequencing method is chosen from pyrosequencing, reversible terminator sequencing, ligation sequencing, nanopore sequencing, and third-generation sequencing.

In some embodiments, sequence data is obtained using a bulk sequencing method, for example, Sanger sequencing or Maxam-Gilbert sequencing.

Single molecule sequencing methods are distinguished from bulk sequencing methods according to whether a single nucleic acid molecule is isolated as part of the sequencing procedure. The nucleic acid molecule may be single- or double-stranded; two annealed nucleic acid strands are considered a single molecule for this purpose. The isolation of the single molecule may occur in a microwell, via use of a nanopore, by direct or indirect attachment in an optically resolvable manner to a substrate such as a microscope slide, or in any other way that allows sequence data to be obtained from the individual molecule. In indirect attachment, the single molecule is attached to the substrate via a linking structure that binds to the single molecule, for example, a protein or oligonucleotide. Notably, methods in which a single molecule is isolated, then amplified, and sequence data is obtained directly from the amplification product(s) are still considered single molecule methods because a single molecule was isolated and served as the ultimate source of the sequence data. (In contrast, in bulk sequencing methods, a nucleic acid sample is used that contains multiple molecules and data is obtained containing signal that originated from multiple molecules.) In some embodiments, single molecule sequencing is performed wherein redundant sequence is obtained from the same molecule. The redundant sequence can be obtained by sequencing at least two direct or inverted repeats within a molecule, or by sequencing the same segment of the molecule more than once. The redundant sequence can be completely redundant or partially redundant with some variation, e.g., due to differences introduced by alteration of base pairing specificity of bases of a certain type, or due to errors that may occur during the sequencing process. In some embodiments, the alteration of base pairing specificity can occur prior to sequencing. In some embodiments, the same molecule is sequenced multiple times, optionally with an intervening treatment that selectively alters base pairing specificity of bases of a certain type occurring between the iterations of sequencing.

Sanger sequencing, which involves using labeled dideoxy chain terminators, is well known in the art; see, e.g., Sanger et al., *Proc Natl Acad Sci USA* 74, 5463-5467 (1997). Maxam-Gilbert sequencing, which involves performing multiple partial chemical degradation reactions on fractions of the nucleic acid sample followed by detection and analysis of the fragments to infer the sequence, is also well known in the art; see, e.g., Maxam et al., *Proc Natl Acad Sci USA* 74, 560-564 (1977). Another bulk sequencing method is sequencing by hybridization, in which the sequence of a sample is deduced based on its hybridization properties to a plurality of sequences, e.g., on a microarray or gene chip; see, e.g., Drmanac, et al., *Nat Biotechnol* 16, 54-58 (1998).

Single molecule sequencing methods are discussed generally, for example, in Kato, *Int J Clin Exp Med* 2, 193-202 (2009) and references therein.

Pyrosequencing, reversible terminator sequencing, and ligation sequencing are considered to be second-generation sequencing methods. Generally, these methods use amplification products generated from a single molecule, which are spatially segregated from amplification products generated from other molecules. The spatial segregation can be implemented by using an emulsion, a picoliter well, or by attachment to a glass slide. Sequence information is obtained via fluorescence upon incorporation of a nucleotide; after acquiring data, the fluorescence of the newly incorporated nucleotide is eliminated and the process is repeated for the next nucleotide.

In pyrosequencing, the pyrophosphate ion released by the polymerization reaction is reacted with adenosine 5' phosphosulfate by ATP sulfurylase to produce ATP; the ATP then drives the conversion of luciferin to oxyluciferin plus light by luciferase. As the fluorescence is transient, no separate step to eliminate fluorescence is necessary in this method. One type of deoxyribonucleotide triphosphate (dNTP) is added at a time, and sequence information is discerned according to which dNTP generates significant signal at a reaction site. The commercially available Roche GS FLX instrument acquires sequence using this method. This technique and applications thereof are discussed in detail, for example, in Ronaghi et al., *Anal Biochem* 242, 84-89 (1996) and Margulies et al., *Nature* 437, 376-380 (2005) (corrigendum at *Nature* 441, 120 (2006)).

In reversible terminator sequencing, a fluorescent dye-labeled nucleotide analog that is a reversible chain terminator due to the presence of a blocking group is incorporated in a single-base extension reaction. The identity of the base is determined according to the fluorophore; in other words, each base is paired with a different fluorophore. After fluorescence/sequence data is acquired, the fluorophore and the blocking group are chemically removed, and the cycle is repeated to acquire the next base of sequence information. The Illumina GA instrument operates by this method. This technique and applications thereof are discussed in detail, for example, in Ruparel et al., *Proc Natl Aced Sci USA* 102, 5932-5937 (2005), and Harris et *Science* 320, 106-109 (2008).

In ligation sequencing, a ligase enzyme is used to join a partially double-stranded oligonucleotide with an overhang to the nucleic acid being sequenced, which has an overhang; in order for ligation to occur, the overhangs must be complementary. The bases in the overhang of the partially double-stranded oligonucleotide can be identified according to a fluorophore conjugated to the partially double-stranded oligonucleotide and/or to a secondary oligonucleotide that hybridizes to another part of the partially double-stranded oligonucleotide. After acquisition of fluorescence data, the ligated complex is cleaved upstream of the ligation site, such as by a type IIs restriction enzyme, for example, BbvI, which cuts at a site a fixed distance from its recognition site (which was included in the partially double stranded oligonucleotide). This cleavage reaction exposes a new overhang just upstream of the previous overhang, and the process is repeated. This technique and applications thereof are discussed in detail, for example, in Brenner et at, *Nat Biotechnol* 18, 630-634 (2000). In some embodiments, ligation sequencing is adapted to the methods of the invention by obtaining a rolling circle amplification product of a circular nucleic acid molecule, and using the rolling circle amplification product as the template for ligation sequencing.

In nanopore sequencing, a single stranded nucleic acid molecule is threaded through a pore, e.g., using an electrophoretic driving force, and sequence is deduced by analyzing data obtained as the single stranded nucleic acid molecule passes through the pore. The data can be ion current data, wherein each base alters the current, e.g., by partially blocking the current passing through the pore to a different, distinguishable degree.

In third-generation sequencing, a slide with an aluminum coating with many small (~50 nm) holes is used as a zero mode waveguide (see, e.g., Levene et at, *Science* 299, 682-686 (2003)). The aluminum surface is protected from attachment of DNA polymerase by polyphosphonate chemistry, e.g., polyvinylphosphonate chemistry (see, e.g., Korlach et al., *Proc Natl Acad Sci USA* 105, 1176-1181 (2008)). This results in preferential attachment of the DNA polymerase molecules to the exposed silica in the holes of the aluminum coating. This setup allows evanescent wave phenomena to be used to reduce fluorescence background, allowing the use of higher concentrations of fluorescently labeled dNTPs. The fluorophore is attached to the terminal phosphate of the dNTPs, such that fluorescence is released upon incorporation of the dNTP, but the fluorophore does not remain attached to the newly incorporated nucleotide, meaning that the complex is immediately ready for another round of incorporation. By this method, incorporation of dNTPs into an individual primer-template complexes present n the holes of the aluminum coating can be detected. See, e.g., Eid et al., *Science* 323, 133-138 (2009).

Sequencing Template; Amount of Sequencing Data Obtained

In some embodiments, sequence data is obtained directly from a circular nucleic acid molecule, that is, by using the circular nucleic acid molecule as a template. The circular nucleic acid molecule used as a template can be a circular pair-locked molecule. In some embodiments, sequence data is obtained from a product nucleic acid molecule that itself was synthesized using a circular nucleic acid molecule as a template; that is, a template from which sequence data is obtained can be a product nucleic acid molecule synthesized from a circular nucleic acid molecule template. In some embodiments, sequence data is obtained from both a circular nucleic acid molecule template and from a product nucleic acid molecule synthesized from the circular nucleic acid molecule template.

In some embodiments, rolling circle amplification, comprising synthesizing a product nucleic acid molecule comprising at least two insert-sample units using the circular nucleic acid molecule as a template, is performed. In some embodiments, the rolling circle amplification comprises synthesizing a product nucleic acid molecule comprising at least 3, 4, 5, 10, 15, 20, 25, 50, or 100 insert-sample units. The use of rolling circle amplification to produce a number of copies of a template is well known in the art; see, e.g., Blanco et al., *J Biol Chem* 264, 8935-8940 (1989) and Banér et al., *Nucleic Acids Res* 26, 5073-5078 (1998). The rolling circle amplification can be performed as part of sequencing in which the circular nucleic acid molecule is the sequencing template, or to synthesize a product nucleic acid molecule which is to be used as a sequencing template.

Regardless of the template, the sequence data obtained according to the methods of the invention comprises at least two repeats of the nucleic acid sample sequence; these at least two repeats can include, in some embodiments, at least one forward repeat of the nucleic acid sample sequence and at least one reverse repeat of the nucleic acid sample sequence. In some embodiments, the sequence data comprise at least 3, 4, 5, 10, 15, 20, 25, 50, or 100 repeats of the nucleic acid sample sequence. In some embodiments, the sequence data comprise at least 2, 3, 4, 5, 10, 15, 20, 25, 50, or 100 forward repeats of the nucleic acid sample sequence. In some embodiments, the sequence data comprise at least 2, 3, 4, 5, 10, 15, 20, 25, 50, or 100 reverse repeats of the nucleic acid sample sequence. In some embodiments, the sequence data comprise at least 2, 3, 4, 5, 10, 15, 20, 25, 50, or 100 each of forward and reverse repeats of the nucleic acid sample sequence.

Calculating Scores

In some embodiments, the methods of the invention comprise calculating scores of the sequences of at least two inserts in the sequence data by comparing the sequences to the known sequence of the insert. In embodiments in which the sequence of the insert is only partially or inexactly known, the known sequence of the nucleic acid insert can comprise ambiguous or unknown positions, for example, through use of ambiguity codes or a position weight matrix.

Comparing the sequences to the known sequence of the insert includes identifying the sequences of at least two inserts in the sequence data. Identifying the sequences can be done in some embodiments by visual inspection, i.e., by a person visually scanning the sequence data and spotting the insert nucleic acid sequences contained therein, or by a computer-aided alignment method. See, e.g.; International Patent Application Publication WO 2009/017678. In some embodiments, identifying the sequences can be done by scanning the sequence data using an algorithm that recognizes the sequences, for example, by calculating scores iteratively or heuristically for multiple positions within the sequence data in order to identify local extrema that correspond most closely to the known sequence of the nucleic acid insert. In some embodiments, identifying the sequence of the at least two nucleic acid inserts is performed simultaneously with calculating the scores, in that both processes can utilize the same score.

In some embodiments, calculating scores comprises performing an alignment using an appropriate alignment algorithm, of which many are known in the art and are readily available, for example, BLAST, MEGABLAST, Smith- Waterman alignment, and Needleman-Wunsch alignment. See. e.g., Altschul et al., *J Mol Biol* 215, 403-410 (1990). Appropriate alignment algorithms include both algorithms allowing gaps and algorithms that do not allow gaps. Alternatively, in some embodiments, calculating scores comprises analyzing the sequences using an algorithm such as running a position weight matrix over the sequences and calculating the sum of the elements of the matrix corresponding to the sequence. In this way, the score can be calculated as the local maximum found by applying the matrix to a sequence read in a stepwise fashion.

In some embodiments, the scores are positively correlated with the closeness of the at least two nucleic acid insert sequences to the known sequence (e.g., the maximum possible score results from an exact match). Such positively correlated scores include, without limitation, percent identity, bit scores, and matching base count.

In some embodiments, the scores are negatively correlated with the closeness of the at least two nucleic acid insert sequences to the known sequence (e.g., the minimum possible score results from an exact match). Such negatively correlated scores include, without limitation, e-value, number of mismatches, number of mismatches and gaps, percent mismatched, and percent mismatched/gapped.

In some embodiments, the scores are calculated on a rate basis. The possible range of scores calculated on a rate basis does not change as a function of the length of the sequences being compared. Examples of scores calculated on a rate basis include, without limitation, percent identity and percent mismatched/gapped.

In some embodiments, the scores are calculated on a count basis. The possible range of scores calculated on a count basis changes as a function of the length of the sequences being compared, Examples of scores calculated on a count basis include, without limitation, bit scores, number of mismatches, number of mismatches and gaps, and matching base count.

Accepting or Rejecting Repeats of the Sequence of the Nucleic Acid Sample; Accepted Sequence Set In some embodiments, the methods of the invention comprise accepting or rejecting repeats of the sequence of the nucleic acid sample in the sequence data according to the scores of one or both of the sequences of the inserts immediately upstream and downstream of the repeat of the sequence of the nucleic acid sample. Thus, in various embodiments, the scores of both the immediately upstream and immediately downstream nucleic acid inserts, the score of either one, or the score of one or the other specifically is/are used to decide whether to accept or reject a nucleic acid sample sequence in the sequence data.

In embodiments in which the scores are positively correlated with the closeness of the at least two nucleic acid insert sequences to the known sequence, scores are required to be greater than, or greater than or equal to, a threshold value in order to accept a sequence. The choice of an appropriate threshold value depends on multiple factors, including the type of score being used, the error rate of the sequencing method, and time and redundancy considerations.

Accepting and rejecting repeats of the sequence of the nucleic acid sample can be implemented in various ways such that at least one accepted repeat is used, and any rejected repeats are not used, to determine the sequence of the nucleic acid sample. Accepting and rejecting repeats may or may not be performed in a concerted manner with compiling an accepted sequence set. For example, the sequences of accepted repeats can be copied as they are accepted into a new data structure, which becomes the accepted sequence set. Or, the sequences of rejected repeats can be deleted or overwritten (e.g., with '0' or 'X' characters that represent null or excluded data) as they are rejected; in this case, once the rejected sequences have been deleted or overwritten, the original data structure has been modified so as to become the accepted sequence set. In these examples, accepting and rejecting repeats is considered to be performed in a concerted manner with compiling an accepted sequence set.

In some embodiments, repeats of the sequence of the nucleic acid sample can be rejected on an additional basis, such as having a length that deviates from the length of other repeats of the sequence of the nucleic acid sample (see, e.g., FIG. 7B). For example, a repeat of the sequence of the nucleic acid sample can be rejected if it deviates to a threshold extent from the mean or median length of the other nucleic acid sample sequences, or of a preliminary version of the accepted sequence set comprising repeats of the sequence of the nucleic acid sample accepted according to the scores of one or both of the sequences of the inserts immediately upstream and downstream of the repeat of the sequence of the nucleic acid sample as described above, which may or may not have the repeat of the sequence of the nucleic acid sample under consideration for possible rejection temporarily removed for calculation of the median or mean length. The threshold extent can be expressed in terms of absolute length, for example, 1, 2, 5, 10, 20, or 50 nucleotides; relative length, for example, 1%, 2%, 5%, 10%, 20%, or 50%; or in terms of a statistical measure, such as standard deviation, for example, 0.5, 1, 1.5, 2, 2.5, 3, 3.5, 4, or 5 standard deviations.

Alternatively, the sequences can be flagged as accepted or rejected, and then after the flagging process is complete, the accepted sequences can be copied into a new data structure, or the rejected sequences can be deleted or overwritten, to generate an accepted sequence set in a non-concerted manner.

The accepted sequence set can be chosen from forms including a single data string, which comprises the at least one accepted repeat of the sequence of the nucleic acid sample and any additional accepted repeats in concatenated form, and a multi-element variable, in which each element represents an accepted repeat of the sequence of the nucleic acid sample or a subpart thereof. In some embodiments, the multi-element variable is chosen from a list, array, hash, and matrix. Any form of data structure allowing for storage of the at least one accepted repeat of the sequence of the nucleic acid sample and subsequent determination of the sequence of the nucleic acid sample is suitable for use.

In embodiments in which the form of the accepted sequence set differs from the form of the raw sequence data (e.g., the raw sequence data is in the form of a string and the accepted sequence set is in the form of a multi-element data structure such as an array), the raw sequence data can be parsed into elements containing repeats, insert-sample units, or sample repeats flanked by the immediately upstream and downstream inserts at a point in the method after the raw sequence data is obtained and before the final accepted sequence set is generated. This parsing step can occur before or after the scoring step discussed above.

Determining the Sequence of the Nucleic Acid Sample; Consensus Sequences; Confidence Levels In some embodiments, the methods comprise determining the sequence of the nucleic acid sample.

The mode of determining the sequence of the nucleic acid sample can be chosen conditionally based on the number of repeats of the nucleic acid sample in the accepted sequence set. For example, when the accepted sequence set contains only one accepted repeat, the sequence of the nucleic acid sample can be determined to be the sequence of the accepted repeat. When the accepted sequence set contains only two, or at least three, accepted repeats, the sequence of the nucleic acid sample can be determined to be the consensus sequence (see below) of the accepted repeats. More options for how the consensus sequence is determined are available when the accepted sequence set contains at least three accepted repeats.

Consensus Sequence

The consensus sequence is determined from an alignment (performed as discussed above, in the "Calculating scores" section) of the accepted repeats; at positions in the alignment where the accepted repeats contain the same base, the consensus sequence contains that base. In some embodiments, at positions in the alignment where the accepted repeats do not contain the same base, the consensus sequence contains the appropriate ambiguity code (e.g., R when the accepted repeats contain A and G at a position). In some embodiments, at positions in the alignment where the accepted repeats do not contain the same base, the consensus sequence contains an N or other symbol indicative of an unknown base. In some embodiments, at positions in the alignment where the accepted repeats do not contain the same base, the consensus sequence contains the base from the accepted repeat that gave a stronger or more robust signal during acquisition of the sequence (e.g., if the raw data were in the form of fluorescence, the base which was called based on brighter fluorescence emission (in some embodiments, after appropriate normalization and/or standardization) is placed in the consensus sequence.

When a consensus sequence is determined from an accepted sequence set containing at least three accepted repeats, the base at each position of the consensus sequence can in some embodiments be determined by majority vote; i.e., the base present at a position in more than half of the accepted repeats is placed at that position in the consensus sequence. When the accepted repeats disagree at a position such that there is no majority vote at that position, the base at that position in the consensus sequence is determined by another method, for example, the plurality vote can be used (i.e., the base most frequently present at a position in of the accepted repeats is placed at that position in the consensus sequence), or one of the procedures discussed in the preceding paragraph can be used.

In some embodiments, when a consensus sequence is determined from an accepted sequence set containing at least three accepted repeats, the base at each position of the consensus sequence can in some embodiments be determined according to the frequency of each base at that position in the accepted repeats. Thus, the consensus sequence can be a probabilistic representation of the likelihood that each base is present at each position in the nucleic acid sample. Such a representation can take the form of a position weight matrix. In some embodiments, the elements of the position weight matrix are the frequencies with which each base was observed at each position in the alignment of the accepted repeats.

In some embodiments, the elements of the position weight matrix are calculated from the frequencies with which each base was observed at each position in the alignment of the accepted repeats; other factors can also be used in this calculation, for example, when some accepted repeat sequences were acquired with stronger or more robust signals during acquisition of the sequence than other repeats, the accepted repeat sequences can be given more weight, and/or the other repeats can be given less weight. The degree to which the weights are modified can be quantitatively determined, based, for example, on the signal strength, or it can be a fixed modification; for example, the weight of bases acquired with a relatively strong signal can be increased by a value such as 50% or 100%, and/or the weight of bases with a relatively weak signal can be reduced by a value such as 33% or 50%.

In some embodiments, the elements of the position weight matrix are values which have been derived from transformed frequencies of each base at each position (possibly weighted as discussed above). Frequencies can be transformed, for example, logarithmically or by exponentiation; in some embodiments, the transformation has the effect of down weighting bases rarely observed at a position and/or up weighting the base or bases commonly observed at a position. For example, if T is present at a position in an alignment of N accepted repeat sequences M times, where N>2 and M<N/2, and C is present every other time (i.e., N−M times), in some embodiments the transformation of these frequencies would result in the weight of T in the position weight matrix being less than NUN (or the percentage corresponding thereto) and/or the weight of C being greater than (N−M)/N (or the percentage corresponding thereto), In some embodiments, the transformation is chosen so as to only up weight the most commonly observed base (or bases in the case of a tie in frequency).

Confidence Levels

In some embodiments, a confidence level is determined for at least one position in the sequence of the nucleic acid sample, A confidence level can be expressed in a number of ways, for example, as an overall base call accuracy value, expressed as a percentage or as a phred score, or as an error rate. In some embodiments, the confidence level is determined from the frequency of the most common base or bases at a position, or of the combined frequency of the bases that are not the most common. In some embodiments, these frequencies are transformed, up weighted, and/or down weighted as discussed above.

Determining a Confidence Level of the Sequence as a Whole; Determining the Sequence of the Nucleic Acid Sample and Confidence Levels in Real Time and/or to a Desired Level of Confidence In some embodiments, the methods of the invention comprise determining a confidence level of the sequence as a whole. The confidence level of the sequence as a whole can be expressed in a number of ways, for example, as an overall base call accuracy value, expressed as a percentage or as a phred score; as an error rate; or as an expected number of errors in the sequence.

Confidence levels from the individual positions, as discussed in the above section, can be used to calculate the confidence level of the sequence as a whole. For example, an overall confidence level can be determined as the arithmetic mean, geometric mean, median, or modal confidence level of the statistical population of confidence levels at each position of the sequence of the nucleic acid sample. In some embodiments, the statistical population of confidence levels at each position of the sequence of the nucleic acid sample is processed prior to calculation of the confidence level of the sequence as a whole, for example, to reject outliers.

In some embodiments, the methods of the invention comprise determining the sequence of the nucleic acid sample and confidence levels in real time. In these embodiments, data acquired in the sequencing step is processed to determine sequence and confidence levels concurrently with the acquisition of additional sequence data, e.g., from additional repeats of a rolling circle amplification product. As the additional sequence data is acquired, both the determined sequence and the confidence levels are updated. In some embodiments, the real time process is continued until a preselected confidence level is reached. The preselected confidence level can be, for example, a base call accuracy of 90%, 95%, 99%, 99.5%, 99.9%, 99.95%, or 99.99%. The preselected confidence level can be for the sequence as a whole or a fraction of the positions in the sequence, and can be chosen from values such as, for example, 50%, 67%, 75%, 80%, 85%, 90%, 95%, 98%, 99%, 99.5%, and 99.9%.

Multiple Samples; Assembling a Contig

In some embodiments, the method comprises repeating the steps of the method using at least one other sample from the same source, species; or strain as the nucleic acid sample that has a sequence, that partially overlaps the sequence of the nucleic acid sample, thereby determining at least one other sequence, and assembling the at least one other sequence with the sequence of the original sample to form a contig. In some embodiments, the method comprises repeating the steps of the method with many samples, so as to generate contigs of sizes greater than 0.5, 1, 2, 5, 10, or 100 kb, or 1, 2, 5, 10, 100, or 1,000 Mb. In some embodiments, the contig represents the complete sequence, or the complete sequence except for heterochromatic or refractory regions, of a nucleic acid molecule, which may be, for example and without limitation, a chromosome, minichromosome, artificial chromosome, viral genome, or extrachromosomal element. Contig assembly can be carried out using methods known in the art.

Modified Bases

In some embodiments, the nucleic acid sample comprises at least one modified base, for example, 5-methylcytosine, 5-bromouracil, uracil, 5,6-dihydrouracil, ribothymine, 7-methylguanine, hypoxanthine, or xanthine. Uracil can be considered a modified base in a DNA strand, and ribothymine can be considered a modified base in an RNA strand. In some embodiments, at least one modified base in the double-stranded nucleic acid sample is paired with a base that has a base pairing specificity different from the preferred partner base(s) of the modified base. This can occur, for example, when one base in a double stranded molecule has undergone a reaction (e.g., due to sporadic oxidation, or exposure to a mutagenizing agent such as radiation or a chemical mutagen) that converted it from one of the standard bases to a modified base that does not have the same preferred partner base(s).

Preferred partner bases are based on Watson-Crick base pairing rules. For example, the preferred partner base of adenine is thymine (or uracil), and vice versa; the preferred partner base of cytosine is guanine, and vice versa. Preferred partner bases of modified bases are generally known to those of skill in the art or can be predicted based on the presence of hydrogen bond donors and acceptors in positions analogous to those of the standard bases. For example, hypoxanthine has a hydrogen bond acceptor (a double-bonded oxygen) in the 6 position of the purine ring, like guanine, and therefore its preferred partner base is cytosine, which has a hydrogen bond donor (an amine group) in the 6 position of the pyrimidine ring. Notably, hypoxanthine can be formed by deamination of adenine. As adenine would normally be paired with thymine in DNA, this deamination reaction can result in a hypoxanthine-thymine pair, in which the modified base hypoxanthine is not paired to its preferred partner base. Cytosine can also be deaminated to form uracil. In the context of DNA, uracil can be considered a modified base, and if it is paired to guanine (as can result from cytosine deamination in normal double-stranded DNA), then this is also a situation where the modified base uracil is not paired to its preferred partner base.

Detection of Modified Bases; Altering the Base Pairing Specificity of Bases of a Specific Type In some embodiments, the methods of the invention comprise altering the base pairing specificity of bases of a specific type. Altering the base pairing specificity of bases of a specific type can comprise specifically altering the base pairing specificity of an unmodified version of a base, e.g., cytosine. In this case, the base pairing specificity of at least one modified form of the base, for example, 5-methylcytosine, is not altered.

Alternatively, altering the base pairing specificity of bases of a specific type can comprise specifically altering the base pairing specificity of a modified version of a base (e.g., 5-methylcytosine), but not the unmodified version of the base (cytosine).

In some embodiments, altering the base pairing specificity of bases of a specific type comprises photochemical transition, which converts 5-methylcytosine (but not unmodified cytosine) to thymine. See, e.g., Matsumura et al., *Nucleic Acids Symp Ser No.* 51, 233-234 (2007), This reaction alters the base pairing specificity of the bases undergoing photochemical transition from guanine to adenine (guanine pairs with 5-methylcytosine while adenine pairs with thymine).

In other embodiments, altering the base pairing specificity of bases of a specific type comprises bisulfite conversion, which converts cytosine (but not 5-methylcytosine) to uracil. See, e.g., Laird et al., *Proc Natl Acad Sci USA* 101, 204-209 (2004), and Zilberman et al., *Development* 134, 3959-3965 (2007). This reaction alters the base pairing specificity of the bases undergoing bisulfite conversion from guanine to adenine (guanine pairs with cytosine while adenine pairs with uracil).

In still other embodiments, modified bases can be detected without an alteration step, such as in cases where the modified base has altered base pairing specificity relative to the unmodified version of the base. Examples of such bases may include 5-bromouracil, uracil, 5,6-dihydrouracil, ribothymine, 7-methylguanine, hypoxanthine, and xanthine. See, e.g., Brown, *Genomes*, $2^{nd}$ Ed., John Wiley & Sons, Inc., New York, N.Y., 2002, chapter 14, "Mutation, Repair, and Recombination," discussing the propensity of 5-bromouracil to undergo keto-enol tautomerization which results in increased pairing to guanine relative to adenine, and the formation of hypoxanthine (which pairs preferentially to cytosine over thymine) by deamination of adenine.

Nucleotide Analog that Discriminates Between a Base and its Modified Form

In some embodiments, sequence data is obtained using at least one nucleotide analog that discriminates between a base and its modified form (a "discriminating analog"; it pairs preferentially with one but not the other of the base and its modified form). The nucleotide analog can be used and detected as though it is a fifth base in addition to the standard four bases, for example, by use of differential labels in reversible terminator sequencing or ligation sequencing, or when it is incorporated in pyrosequencing, in which nucleotides can be added one at a time and then washed away. In some embodiments, the discriminating analog is added before its corresponding natural nucleotide (e.g., in pyrosequencing) or provided in a concentration ranging from 10 to 100-fold higher than the concentration of its cognate natural nucleotide (e.g., in reversible terminator sequencing). For example, the discriminating analog can be an analog of deoxyguanosine triphosphate that discriminates between cytosine and 5-methylcytosine (e.g., it will pair with cytosine but not 5-methylcytosine); the analog can be provided at a concentration ranging from 10 to 100-fold higher than the concentration of deoxyguanosine triphosphate. In this way, the analog should generally be incorporated opposite the version of the base it preferentially pairs with, but the natural base should generally be incorporated opposite the version of the base that the analog does not preferentially pair with.

Examples of discriminating analogs can be found in U.S. Pat. No. 7,399,614, and include, for instance, the following molecules, which discriminate between unmodified cytosine and 5-methylcytosine, in that they preferentially pair with the former:

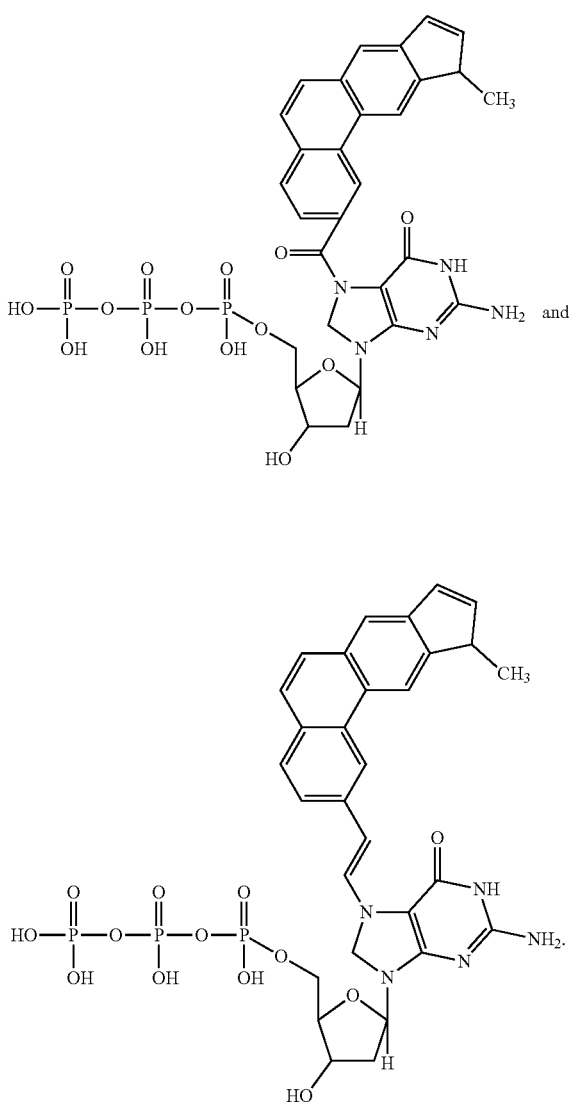

These molecules are referred to as Discriminating Analog 1 and Discriminating Analog 2, respectively.

Determining the Positions of Modified Bases in the Nucleic Acid Sample

In some embodiments, the methods of the invention comprise determining the positions of modified bases in the nucleic acid sample. These embodiments comprise (i) providing the nucleic acid sample in double-stranded form; (ii) converting the nucleic acid sample into a circular pair-locked molecule, wherein the circular pair-locked molecule comprises forward and reverse repeats of the sequence of the nucleic acid sample and two nucleic acid inserts having known sequences, which may be identical or non-identical; (iii) optionally altering the base-pairing specificity of bases of a specific type in the circular pair-locked molecule; (iv) then, obtaining sequence data templated by the forward and reverse repeats of the circular pair-locked molecule or by a complementary sequence thereof; and (v) determining the positions of the modified bases in the nucleic acid sample using the sequence data of at least the forward and reverse repeats or copies thereof. Notably, sequence templated by a forward repeat will have the same sense as the reverse repeat (and vice versa), but may or may not be completely identical to the reverse repeat; differences can result from the forward repeat containing bases that can pair to a base other than the corresponding base in the reverse repeat. An example of such a situation is if the forward repeat in a cPLM contains 5-bromouracil which had been paired to an adenine in the reverse strand but templates the addition of a guanine in a sequencing-by-synthesis reaction.

Figure 5A:
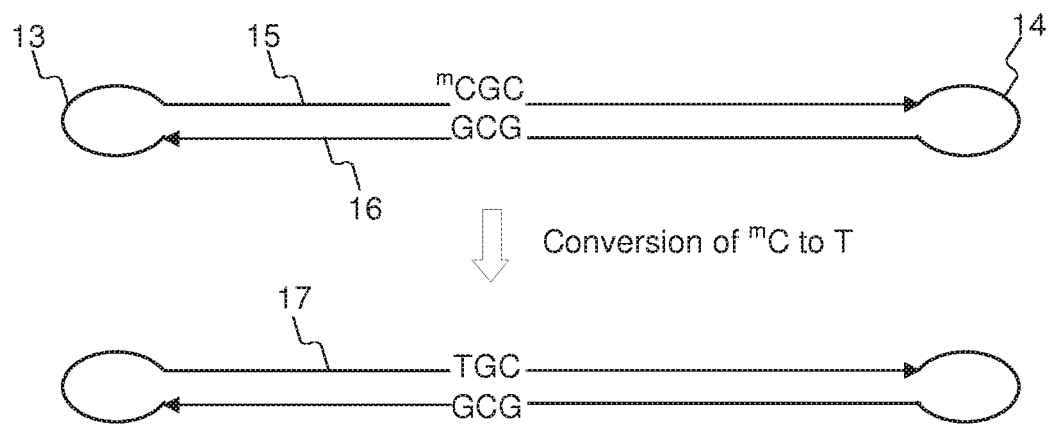
FIG. 5A. A circular pair-locked molecule containing inserts 13 and 14, a forward strand 15 containing at least one 5-methylcytosine ($^{m}C$) residue, and a reverse strand 16 is subjected to treatment, such as photochemical transition, to convert $^{m}C$ to T, resulting in converted forward strand 17. The complementary nucleotide in the reverse strand is unaffected, resulting in a G-T wobble pair. ($^{m}C$ residues in the reverse strand, if present, would be converted by the treatment.) FIG. 5B. A circular pair-locked molecule containing inserts 13 and 14, a forward strand 15 containing at least one 5-methylcytosine ($^{m}C$) residue, and a reverse strand 16 is subjected to treatment, such as bisulfite conversion, to convert C (but not C) to U, resulting in converted forward strand 39 and converted reverse strand 40. The nucleotides complementary to the converted nucleotides are unaffected, resulting in G-U wobble pairs.
Figure 5B:
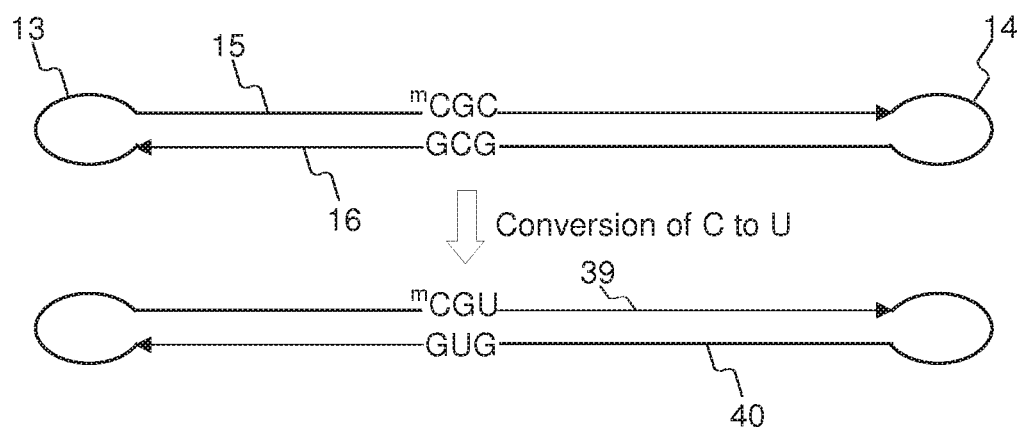
Figure 6A:
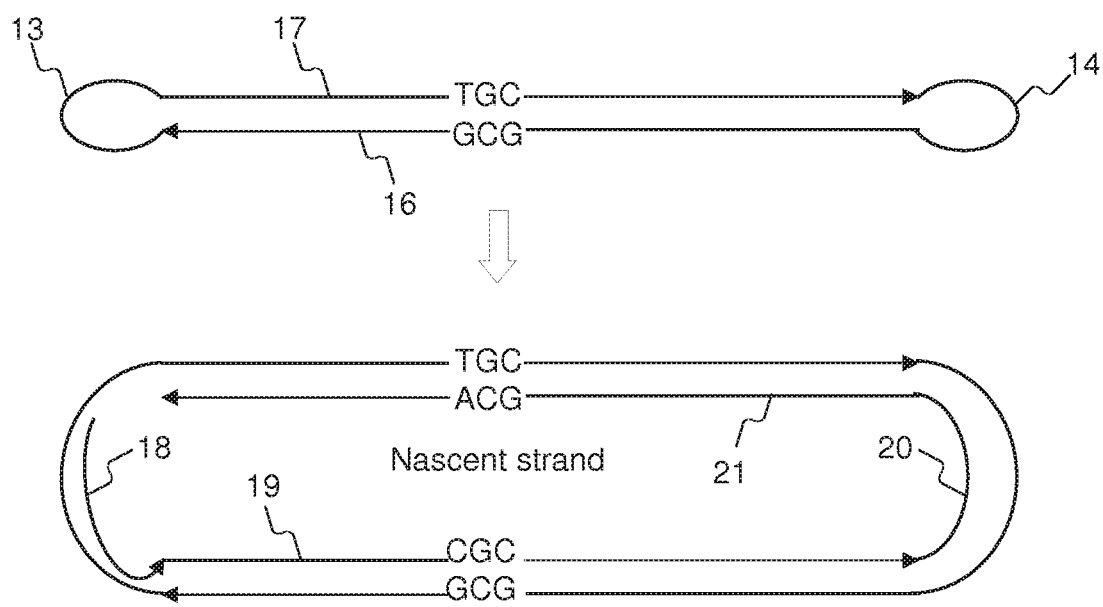
FIG. 6A. A primer 18 is annealed to the converted circular pair-locked molecule of FIG. 5A and extended by a polymerase, resulting in synthesis of a strand with segments 19, 20, and 21, complementary to the sequences of 16, 14, and 17, respectively.
Figure 6B:
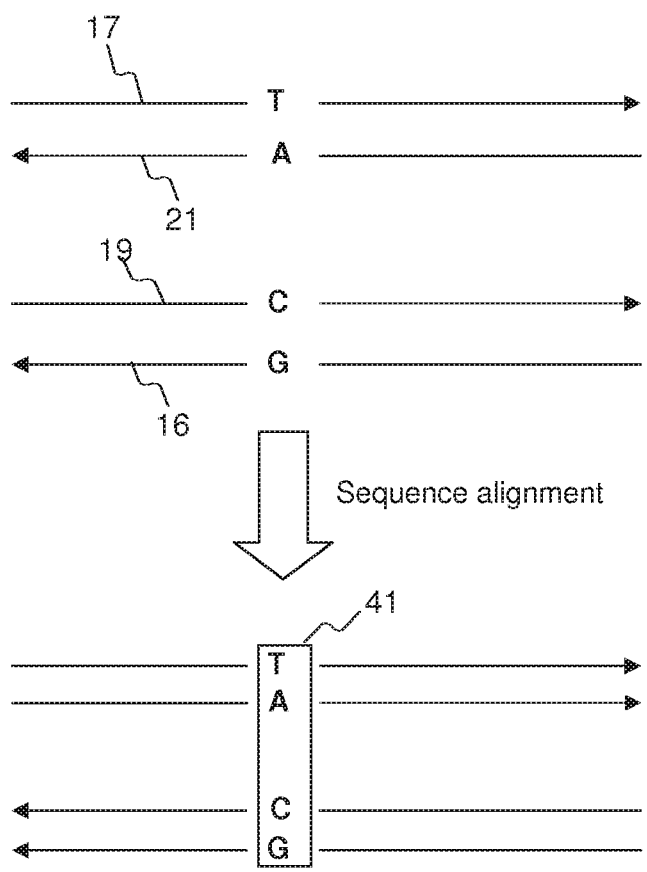
FIG. 6B. Sequence is obtained comprising at least two repeats: at least one of a repeat of the sample 17 and a repeat of the newly synthesized complement of the forward strand 21; and at least one of a repeat of the newly synthesized complement of the reverse strand 19 and a repeat of the reverse strand 16. These repeats are aligned; a position 41 at which there is disagreement among the repeats signifies that a base was modified at that position. Depending on the type of modification used, the bases originally present at the corresponding position of the nucleic acid sample can be determined. In this example, where the circular pair locked molecule has been modified by conversion of $^{m}C$ to T (see FIG. 5A), the disagreement indicates that a $^{m}C$ was present in the nucleic acid sample in the forward strand at position 41; the logic is that at a position where the sequences disagree, the base which is the product of the conversion reaction, T, has replaced the substrate of the conversion reaction, $^{m}C$, which was present in the nucleic acid sample.

Sequence data are obtained comprising at least two repeats: at least one of a repeat of the sample (e.g., the repeat labeled 17 in FIG. 5A) and a repeat of the newly synthesized complement of the forward strand (e.g., the repeat labeled 21 in FIG. 6A); and at least one of a repeat of the newly synthesized complement of the reverse strand (e.g., the repeat labeled 19 in FIG. 6A) and a repeat of the reverse strand (e.g., the repeat labeled 16 in FIG. 6A). These repeats are aligned. The alignment can be performed using any appropriate algorithm, as discussed above. A position at which there is disagreement among the repeats (e.g., the position labeled 41 in FIG. 6B) signifies that a base in the nucleic acid sample at that position underwent alteration of its base pairing specificity. Depending on the type of modification, modified base, and/or discriminating analog used in the process or present in the sample, the bases originally present at the corresponding position of the nucleic acid sample can be determined.

For example, where the circular pair locked molecule has been altered by conversion of $^mC$ to T (see FIG. 5A), the disagreement indicates that a $^mC$ was present in the nucleic acid sample at the position that is a T or complementary to an A in one read, and is a C or complementary to a G in another read; the logic is that at a position where the sequences disagree, the base which is the product of the conversion reaction, T, has replaced the substrate of the conversion reaction, $^mC$, which was present in the nucleic acid sample.

In another example, where the circular pair locked molecule has been altered by conversion of C to U, the disagreement indicates that a C was present in the nucleic acid sample at the position occupied by that is a U or T, or is complementary to an A in one read, and is a C or complementary to a G in another read; the logic is that at a position where the sequences disagree, the base which is the product of the conversion reaction, U (which may be read by the sequencing system as a T), has replaced the substrate of the conversion reaction, C, which was present in the nucleic acid sample. As $^mC$ residues would not be changed by conversion of C to U, the positions where the reads are in agreement in showing C at a position and/or G as its complement indicate that $^mC$ was present at this position in the original sample.

In embodiments in which a discriminating analog was used as discussed above, the presence of the base it preferentially binds to can be inferred in the original sequence at the position of the original sequence corresponding to the position where the discriminating analog appears.

System/Computer Readable Medium

In some embodiments, the invention relates to a system comprising a sequencing apparatus operably linked to a computing apparatus comprising a processor, storage, bus system, and at least one user interface element. The user interface element can be chosen from a display, a keyboard, and a mouse. In some embodiments, the system comprises at least one integrated circuit and/or at least one semiconductor.

In some embodiments, the sequencing apparatus is chosen from sequencing apparatuses configured to perform at least one of the sequencing methods discussed above.

In some embodiments, the display can be a touch screen, serving as the sole user interface element. The storage is encoded with programming comprising an operating system, user interface software, and instructions that, when executed by the processor on a system comprising a sequencing apparatus operably linked to a computing apparatus comprising a processor, storage, bus system, and at least one user interface element, optionally with user input, perform a method of the invention as described above. In some embodiments, the storage further comprises sequence data, which can be in any of the forms discussed above, for example, raw sequence data, an accepted sequence set, a consensus sequence, etc.

In some embodiments, the storage and all of its contents are located within a single computer. In other embodiments, the storage is divided between at least two computers, for example, computers linked via a network connection. In some embodiments, the user interface is part of one computer which is in communication with at least one other computer comprising at least one component of the system, for example, the processing software.

In some embodiments, output of a system or a method executed by a processor results in an indication that there is a modified base in at least one position in a nucleic acid sample. The indication can be in any number of forms, for example, a list of the modified positions in the sequence, a textual or graphical representation of the sequence wherein the modified positions are highlighted or marked, such as with an asterisk or similar character or with bold, italic, or underline formatting, colored text, or a depiction of the chemical structure of the nucleic acid including the structure of the modified base.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Example 1: Rolling Circle Amplification of a Synthetic Circular Pair-Locked Molecule Four oligodeoxyribonucleotides were provided, as shown in Table 1.

TABLE 1

Oligonucleotide sequences

| Name | Sequence | SEQ ID NO |
|---|---|---|
| CPLM-1 | CGACTTATGCATTTGGTATCTGCGCTCTGC ATATTTAAATGGAAGGAGATAGTTAAGGATA AGGGCAGAGCGCAGATAC | 1 |
| CPLM-2 | CAAATGCATAAGTCGTGTCTTACCGGGTTG ATAGCGGCCGCTCGGAGAAAAGAAGTTGG ATGATGCAACCCGGTAAGACA | 2 |
| pS-T1 | CCTTATCCTTAACTATCTCCTT | 3 |
| pS-T2 | TAGCGGCCGCTCGGAGAAAAG | 4 |

CPLM-1 and CPLM-2 were phosphorylated in separate 50 µL reactions in which 30 µL of 10 µM oligodeoxyribonucleotide (final concentration) was treated with 1 µL of 10 U/µL T4 polynucleotide kinase (New England Biolabs ("NEB") Cat. No. M0201S), in the presence of 5 µL 10×T4 ligase buffer (NEB; the 10× stock buffer contains 10 mM ATP). 14 µL ddH$_2$O were added to give a final volume of 50 µL (see Table 2). The reactions were incubated at 37° C. for 30 min, followed by enzyme inactivation at 65° C. for 20 min.

TABLE 2

Phosphorylation reaction conditions (volumes in µL)

| Reagent | 5'P-CPLM-1 | 5'P-CPLM-2 |
|---|---|---|
| 10 uM CPLM-1 | 30 | 0 |
| 10 uM CPLM-2 | 0 | 30 |
| 10 u/uL T4 PNK | 1 | 1 |
| 10 × T4 Ligase buffer | 5 | 5 |
| ddH$_2$O | 14 | 14 |
| Total volume | 50 | 50 |

The concentration of phosphorylated CPLM-1 and CPLM-2 (5'P-CPLM-1 and 5'P-CPLM-2, respectively) from the above reactions was adjusted to 6 µM.

Phosphorylated CPLM-1 and CPLM-2 were then denatured at 95° C. for 5 min, then placed on ice and mixed with buffer, ddH$_2$O; and T4 ligase (NEB, Cat. No. M0202S) to produce circular pair-locked molecules, as shown in Table 3. The ligation occurred at 25° C., and 18 µL aliquots were removed at 10, 30 and 60 min. A negative control with no ligase was run in parallel (L0 column in Table 3).

TABLE 3

Ligation reaction conditions

| Reagent | L0 | L3 |
|---|---|---|
| 6 µM 5'P-CPLM-1 | 9 | 9 |
| 6 µM 5'P-CPLM-2 | 9 | 9 |
| 400 u/µL T4 Ligase | 0 | 3 |
| 10 × buffer | 6 | 6 |
| ddH₂O | 36 | 33 |
| Total volume | 60 | 60 |

The ligation products were combined with pS-T1 and/or pS-T2 primers, dNTPs, RepliPHIT™ Phi29 DNA polymerase (Epicentre, Cat, No. PP031010), and an appropriate 10× reaction buffer RepliPHI Phi29 DNA Polymerase buffer as shown in Table 4.

TABLE 4

Rolling circle amplification of circular pair-locked molecules

| | Controls | | 2-primed | | 1-primed | |
|---|---|---|---|---|---|---|
| Reagent | C1 | C2 | L0 | L3 | L0 | L3 |
| 10 mM dNTP | 5 | 5 | 5 | 5 | 5 | 5 |
| 10 µM pS-T1 primer | 0 | 0 | 6 | 6 | 0 | 0 |
| 10 µM pS-T2 primer | 0 | 0 | 6 | 6 | 6 | 6 |
| 1 × L0_10, 30, 60 min | 1 | 0 | 1 | 0 | 1 | 0 |
| 1 × L3_10, 30, 60 min | 0 | 1 | 0 | 1 | 0 | 1 |
| 1000 u/µL phi29 polymerase | 1 | 1 | 1 | 1 | 1 | 1 |
| 10 × buffer | 5 | 5 | 5 | 5 | 5 | 5 |
| ddH₂O | 38 | 38 | 26 | 26 | 32 | 32 |
| Total volume | 50 | 50 | 50 | 50 | 50 | 50 |

The reactions were assembled without Phi29 polymerase, denatured at 95° C. for 5 min, and placed on ice for 5 min. Phi29 polymerase was added followed by incubation at 30° C. for 18 hours.

5 µL samples of reaction products were mixed with 1 µL 6× loading dye (0.03% bromophenol blue, 0.03% xylene cyanol FF, 60% glycerol, 100 mM Tris-EDTA (pH 7.6)), heated at 95° C. for 10 min, and then placed on ice immediately. A second set of reaction product samples was treated identically except that 1% SDS was added as well.

Samples were loaded into a 0.7% agarose gel in 1×TAE buffer and electrophoresed at 135 V for 28 min. DNA was visualized using GelRed™ precast gel staining (Biotium, Cat. No.; 41003 GelRed™ Nucleic Acid Gel Stain, diluted 10,000× in water). The gel is shown in FIG. 9. Rolling circle amplification products with apparent molecular weights greater than 10 kb were observed in the samples from reactions using L3 ligation reaction products and both pS-T1 and pS-T2 primers, but not the samples using the L0 controls or the samples that lacked a primer. The samples using L3 ligation reaction products and both pS-T1 and pS-T2 primers that were treated with SDS showed greater retention of product in the wells, consistent with denaturation of secondary structure in the RCA products.

Example 2. Simulation of Detection of Methylation Using Conversion of C to U by Bisulfite Treatment with a Linear Pair-Locked Molecule Determination of the sequence and 5-methylcytosine positions of a hypothetical duplex DNA fragment using conversion of C residues to U residues by bisulfite treatment is simulated as follows. The general scheme of this Example is illustrated in FIG. 12. The sequence of the DNA is shown below.

```
         DNA sample (methylated C marked as ᵐC)
5'-AGATGTGGAᵐCGGGGTGGGᵐCGGAGGTGGGTTGGGGC-3'  (SEQ ID NO: 5)
   ||||||||/ ||||||||/ ||||||||||||||||||
3'-TCTACACCTGᵐCCCCACCCGᵐCCTCCACCCAACCCCG-5'  (SEQ ID NO: 6)
```

The two strands are connected by ligation to a linker sequence (represented as "nnnn") to give the following product. The linker sequence is suitable for use as a sequencing primer.

```
                                          (SEQ ID NO: 7)
3'-TCTACACCTGᵐCCCCACCCGᵐCCTCCACCCAACCCCGnnnnCGGGG
TTGGGTGGAGGᵐCGGGTGGGGᵐCAGGTGTAGA-5'
```

Additionally, a linear flap of known sequence (not shown) is attached to each end of the molecule of SEQ ID NO:7. The flap at the 3' end is suitable for primer binding for sequencing or replication. The complement of the flap at the 5' end is suitable for primer binding for sequencing or replication.

The product is treated with sodium bisulfite, resulting in the conversion of cytosine (but not 5-methylcytosine) residues to uracil, giving the following product. The newly formed uracil residues are bolded and marked with asterisks above the bases.

```
                                          (SEQ ID NO: 8)
    *  * **   *** ***  * **  ***   ***          *
3'-TUTAUAUUTGᵐCUUUAUUUGᵐCUTUUAUUUAAUUUUGnnnnUGGGG
TTGGGTGGAGGᵐCGGGTGGGGᵐCAGGTGTAGA-5'
```

A complementary strand (labeled SEQ ID NO: 9 below) is synthesized via DNA replication involving annealing of a primer to the flap added to the 3' end.

```
3'-TUTAUAUUTGCUUUAUUUGCUTUUAUUUAAUUUUGnnnnUGGGGTTGGGTGGAGGCGGGT
   ||||||||||||||||||||||||||||||||||||||||||||||||||||||||||||
5'-AAATATAAACGAAATAAACGAAATAAATTAAAACnnnnACCCCAACCCACCTCCGCCCA GGGGCAGGTGTAGA-5'  (SEQ ID NO: 8)
||||||||||||||
CCCCGTCCACATCT-3'  (SEQ ID NO: 9)
```

The above duplex is sequenced in both directions; sequencing intermediates are shown below. The nascent strand, whose sequence is being obtained, is SEQ ID NO: 10 in reaction a and SEQ ID NO: 11 in reaction b.

```
sequencing reaction a
5'-AAATATAAACGAAATAAACGAAAATAAATTAAAACnnnnACCCCAACCCACCTCCGCCCA
                                    ||||||||||||||||||||||||||
                                 3'-nnnnTGGGGTTGGGTGGAGGCGGGT CCCCGTCCACATCT-3'   (SEQ ID NO: 9)
||||||||||||||
GGGGCAGGTGTAGA-5'   (SEQ ID NO: 10)

Sequencing reaction b
5'-AAATATAAACGAAATAAACGAAAATAAATTAAAACnnnn-3'   (SEQ ID NO: 11)
   |||||||||||||||||||||||||||||||||||||||
3'-TUTAUAUUTGCUUUAUUUGCUUUUAUUUAAUUUUGnnnnUGGGGTGGGTGGAGGCGGGT

GGGGCAGGTGTAGA-5*   (SEQ ID NO: 8)
```

Thus, the reads predicted to be obtained from these reactions contain the following sequences.

a:
(SEQ ID NO: 10)
5'-AGATGTGGACGGGGTGGGCGGAGGTGGGTTGGGGTnnnn-3' b:
(SEQ ID NO: 11)
5'-AAATATAAACGAAATAAACGAAAATAAATTAAAACnnn-3'

The sequence of the original sample, including cytosine methylation status, is determined by applying the following rules, summarized in Table 5. The forward strand of the original sequence is the strand with the same sense as the two reads.

At positions where read a and read b both have A, the forward strand of the original sequence also has A, and the reverse strand has T. At positions where read a and read b both have T, the forward strand of the original sequence also has T, and the reverse strand has A.

When read a and read b both have C, then the forward strand of the original sequence has $^m$C, and the reverse strand has G. When read a and read b both have G, then the forward strand of the original sequence has G, and the reverse strand has $^m$C.

When one read has G at a position where the other read has A, the forward strand of the original sequence has G, and the reverse strand has C.

When one read has T at a position where the other read has C, the forward strand of the original sequence has C, and the reverse strand has G.

Reads a and b are matched to column 1 and 2 in Table 5 according to which read contains G and T residues at the positions where the reads differ; in this example, read a corresponds to column 1.

TABLE 5

| Bisulfite treatment methylation status determination rules | | | |
|---|---|---|---|
| Sequencing | | Original sequence | |
| reads | | Forward strand | Reverse Strand |
| 1 | 2 | (5' => 3') | (3' => 5') |
| A | A | A | T |
| T | T | T | A |
| C | C | C methylated | G |
| G | G | G | C methylated |
| G | A | G | C |
| T | C | C | G |

Application of the above rules to SEQ ID NOs: 10 and 11 results in recovery (after removal of the linker sequence nnnn) of the original sequences, i.e., SEQ ID NOs: 5 and 6. An alignment of reads a and b with the forward strand of the original sequence is shown in FIG. 10A.

Example 3. Simulation of Detection of Methylation Using Conversion of mC to T by Photochemical Transition with a Linear Pair-Locked Molecule Determination of the sequence and 5-methylcytosine positions of a hypothetical duplex DNA fragment using conversion of $^m$C to T by photochemical transition is simulated as follows. The general scheme of this Example is shown in FIG. 13. The sequence of the DNA is shown below.

```
DNA sample (methylated C marked as ᵐC)
5'-AGATGTGGAᵐCGGGGTGGGᵐCGGAGGTGGGTTGGGGC-3'   (SEQ ID NO: 5)
   ||||||||/  ||||||||/  ||||||||||||||||
3'-TCTACACCTGᵐCCCCACCCGᵐCCTCCACCCAACCCCG-5'   (SEQ ID NO: 6)
```

The two strands are connected by ligation to a linker sequence (represented as "nnnn") to give the following product. The linker sequence is suitable for use as a sequencing primer. Linear flaps (not shown) are also attached to the 3' and 5' ends of this molecule.

(SEQ ID NO: 7)
```
3'-TCTACACCTGᵐCCCCACCCGᵐCCTCCACCCAACCCCGnnnnCGGGG
   TTGGGTGGAGGᵐCGGGTGGGGᵐCAGGTGTAGA-5'
```

The product is treated with light so as to photochemically convert 5-methylcytosine (but not cytosine) residues to thymine, giving the following product. The newly formed thymine residues are bolded and marked with asterisks above or below the bases.

(SEQ ID NO: 12)
```
              *           *                             *
3'-TCTACACCTGTCCCACCCGTCTCCACCCAACCCCGnnnnCGGGGTTGGGTGGAGGTGGG
GGGGTAGGTGTAGA-5'
    *
```

A complementary strand (labeled SEQ ID NO: 13 below) is synthesized via DNA replication using a primer that binds to the flap attached to the 3' end of the molecule.

```
3'-TCTACACCTGTCCCACCCGTCTCCACCCAACCCCGnnnnCGGGGTTGGGTGGAGGTGGG
   |||||||||||||||||||||||||||||||||||||||||||||||||||||||||
5'-AGATGTGGACAGGGTGGGCAGAGGTGGGTTGGGGCnnnnGCCCCAACCCACCTCCACCC GGGGTAGGTGTAGA-5' (SEQ ID NO: 12)
||||||||||||||
CCCCATCCACATCT-3' (SEQ ID NO: 13)
```

The above duplex is sequenced in both directions as in Example 2 above, obtaining the following reads.

Read a:

(SEQ ID NO: 14)
5'-AGATGTGGATGGGGTGGGTGGAGGTGGGTTGGGGC-3'

Read b:

(SEQ ID NO: 15)
5'-AGATGTGGACAGGGTGGGCAGAGGTGGGTTGGGGC-3'

The sequence of the original sample, including cytosine methylation status, is determined by applying the following rules, summarized in Table 6. The forward strand of the original sequence is the strand with the same sense as the two reads.

At positions where read a and read b both have A, the forward strand of the original sequence also has A, and the reverse strand has T. At positions where read a and read b both have T, the forward strand of the original sequence also has T, and the reverse strand has A.

When read a and read b both have C, then the forward strand of the original sequence has C, and the reverse strand has G. When read a and read b both have G, then the forward strand of the original sequence has G, and the reverse strand has C.

When one read has G at a position where the other read has A, the forward strand of the original sequence has G, and the reverse strand has $^m$C.

When one read has T at a position where the other read has C, the forward strand of the original sequence has $^m$C, and the reverse strand has G.

Reads a and b are matched to column 1 and 2 in Table 6 according to which read contains G and T residues at the positions where the reads differ; in this example, read a corresponds to column 1.

TABLE 6

Photochemical transition methylation status determination rules

| Sequencing reads | | Original sequence | |
|---|---|---|---|
| 1 | 2 | Forward strand (5' => 3') | Reverse strand (3' => 5') |
| A | A | A | T |
| T | T | T | A |
| C | C | C | G |
| G | G | G | C |
| G | A | G | C methylated |
| T | C | C methylated | G |

Application of the above rules to SEQ ID NOs: 14 and 15 results in recovery (after removal of the linker sequence nnnn) of the original sequences, i.e., SEQ ID NOs: 5 and 6. An alignment of reads a and b with the forward strand of the original sequence is shown in FIG. 10B.

a →

(SEQ ID NO: 14)
5'-AGATGTGGATGGGGTGGGTGGAGGTGGGTTGGGGC-3' b →

(SEQ ID NO: 15)
5'-AGATGTGGAGAGGGTGGGCAGAGGTGGGTTGGGGC-3' r →

(SEQ ID NO: 5)
5'-AGATGTGGA$^m$CGGGGTGGG$^m$CGGAGGTGGGTTGGGGC-3' (r_a)

(SEQ ID NO: 6)
5'-TCTACACCTG$^m$CCCCACCCG$^m$CCTCCACCCAACCCCG-5' (r_b)

Example 4: Comparison of the Accuracy of Simulated Single Read and Multiple Read Sequencing The sequence of an assembled *Escherichia coli* genome, GenBank accession No. U00096, length 4639675 bp, was downloaded from GenBank. Randomly selected fragments with lengths ranging from 500 bp to 2000 bp were extracted from this sequence. These fragments were designated master sequences.

Five subsequences were generated from the master sequences by computationally introducing deletion and misreading errors at defined rates, as shown in Table 7.

The five subsequences, containing errors, were subjected to a multiple sequence comparison analysis using the CLUSTALW algorithm (default settings). The results of the CLUSTALW analysis were used as input for the program "cons" of the EMBOSS package in order to obtain a consensus sequence. The program "cons" is described in Rice et al., *Trends Genet* 16, 276-277 (2000), and Mullan et al., *Brief Bioinform* 3, 92-94 (2002).

The first subsequence and the consensus sequence were each compared to the master sequence, and the frequencies of gaps and misreads were tabulated; see Table 7. The results demonstrated that forming a consensus sequence using multiple reads reduced the frequency of misreads and gaps at each of the various error rates that was tested. For each set of deletion and misreading error rates, a single simulated read and a consensus sequence determined from 5 simulated reads were aligned against the master sequence. The number and percentage of misread and gapped positions were determined as a fraction of the positions in the alignment.

TABLE 7

Accuracy of consensus sequences determined from 5 simulated reads compared to individual reads at varying error rates

| Rate of Introduced Errors | Length of Master (nt) | Single vs. Master Misreads | Single vs. Master Gaps | Consensus vs. Master Misreads | Consensus vs. Master Gaps |
|---|---|---|---|---|---|
| 5% Deletion | 816 | 53/816 | 47/816 | 8/817 | 5/817 |
| 1% Misreading | | (6.5%) | (5.8%) | (1.0%) | (0.6%) |
| 5% Deletion | 1,565 | 90/1565 | 74/1565 | 9/1565 | 4/1565 |
| 2% Misreading | | (5.8%) | (4.7%) | (1.0%) | (0.3%) |
| 1% Deletion | 1,589 | 401/1602 | 41/1602 | 90/1593 | 5/1593 |
| 30% Misreading | | (25.0%) | (2.6%) | (5.6%) | (0.3%) |
| 1% Deletion | 760 | 182/764 | 11/764 | 47/761 | 1/861 |
| 30% Misreading | | (23.8%) | (1.4%) | (6.2%) | (0.1%) |

Example 5. Simulation of Determination of Sequence Using a cPLM

A double stranded nucleic acid sample is provided as in Example 2. The forward and reverse strands of the sample are locked together by ligation of an insert that forms a hairpin to each end of the molecule as shown in the cPLM construction step of FIG. 14 to form a circular pair-locked molecule. A single molecule sequencing by synthesis reaction is performed using a primer that binds to one of the inserts. Sequence data is obtained that comprises at least one sequence of the forward strand of the sample and at least one sequence of the reverse strand of the sample. The sequence data is analyzed by comparing the sequences of the forward and reverse strands of the circular pair-locked molecule to determine the sequence of the nucleic acid sample according to Table 8.

TABLE 8

CPLM sequence determination rules

| Acquired sequence | | Original sequence | |
|---|---|---|---|
| Templated by forward strand | Templated by reverse strand | Forward strand (5' => 3') | Reverse strand (3' => 5') |
| A | T | A | T |
| T | A | T | A |
| C | G | C | G |
| G | C | G | C |

Note: in Table 8 and Tables 9-11 below, the acquired sequence templated by the forward strand corresponds to the upper line of sequencing data (i.e., the sequence shown beneath the arrow labeled "Sequencing" and above the arrow labeled "Sequence analysis") in FIGS. 14-17, respectively. Similarly, the acquired sequence templated by the reverse strand corresponds to the lower line of sequencing data in FIGS. 14-17, respectively.

Example 6. Simulation of Detection of Methylation Using Conversion of C to U by Bisulfite Treatment with a Circular Pair-Locked Molecule The general scheme of this Example is shown in FIG. 15. A double stranded nucleic acid sample comprising at least one 5-methylcytosine is provided as in Example 2. A circular pair-locked molecule is formed as in Example 5. Bisulfite conversion is performed as in Example 2. Sequence data is obtained as in Example 5. The sequence data is analyzed by comparing the sequences of the forward and reverse strands of the circular pair-locked molecule to determine the sequence of the nucleic acid sample and the position of the at least one 5-methylcytosine according to the rules in Table 9.

TABLE 9

CPLM/bisulfite treatment sequence determination rules

| Acquired sequence | | Original sequence | |
|---|---|---|---|
| Templated by reverse strand | Templated by forward strand | Forward strand (5' => 3') | Reverse strand (3' => 5') |
| A | T | A | T |
| T | A | T | A |
| C | A | C | G |
| A | C | G | C |
| C | G | G | C methylated |
| G | C | C methylated | G |

Example 7. Simulation of Detection of Methylation Using Conversion of mC to T by Photochemical Transition with a Circular Pair-Locked Molecule The general scheme of this Example is shown in FIG. 16. A double stranded nucleic acid sample comprising at least one 5-methylcytosine is provided as in Example 3. A circular pair-locked molecule is formed as in Example 5. Photochemical transition is performed as in Example 3. Sequence data is obtained as in Example 5. The sequence data is analyzed by comparing the sequences of the forward and reverse strands of the circular pair-locked molecule to determine the sequence of the nucleic acid sample and the position of the at least one 5-methylcytosine according to the rules in Table 10.

TABLE 10

CPLM/photochemical transition sequence determination rules

| Acquired sequence | | Original sequence | |
| --- | --- | --- | --- |
| Templated by reverse strand | Templated by forward strand | Forward strand (5' => 3') | Reverse strand (3' => 5') |
| A | T | A | T |
| T | A | T | A |
| C | G | C | G |
| G | C | G | C |
| C | A | G | C methylated |
| A | C | C methylated | G |

Example 8. Simulation of Detection of 5-Bromouracil Using a Circular Pair-Locked Molecule The general scheme of this Example is shown in FIG. 17. A double stranded nucleic acid sample comprising at least one 5-bromouracil is provided. A circular pair-locked molecule is formed as in Example 5. Sequence data is obtained as in Example 5. The sequence data is analyzed by comparing the sequences of the forward and reverse strands of the circular pair-locked molecule to determine the sequence of the nucleic acid sample and the position of the at least one 5-bromouracil according to the rules in Table 11.

TABLE 11

CPLM/5-bromouracil sequence determination rules

| Acquired sequence | | Original sequence | |
| --- | --- | --- | --- |
| Templated by reverse strand | Templated by forward strand | Forward strand (5' => 3') | Reverse strand (3' => 5') |
| A | T | A | T |
| T | A | T | A |
| C | G | C | G |
| G | C | G | C |
| G | T | A | 5-bromouracil |
| T | G | 5-bromouracil | A |

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. The recitation of series of numbers with differing amounts of significant digits in the specification is not to be construed as implying that numbers with fewer significant digits given have the same precision as numbers with more significant digits given.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of determining the sequence of a nucleic acid sample comprising:
   a. obtaining sequence data from a circular nucleic acid molecule comprising at least one insert-sample unit comprising a nucleic acid insert and the nucleic acid sample, wherein
      (i) the insert has a known sequence,
      (ii) the sequence data comprises sequences from at least two insert-sample units, including at least two repeats of the sequence of the nucleic acid sample, and
      (iii) a nucleic acid molecule is produced that comprises at least two insert-sample units;
   b. calculating scores of the sequences of at least two inserts of the sequence data of step (a) by comparing the sequences to the known sequence of the insert;
   c. accepting or rejecting at least two of the repeats of the sequence of the nucleic acid sample of the sequence data of step (a) according to the scores of one or both of the sequences of the inserts immediately upstream and downstream of the repeat of the sequence of the nucleic acid sample;
   d. compiling an accepted sequence set comprising at least one repeat of the sequence of the nucleic acid sample accepted in step (c); and
   e. determining the sequence of the nucleic acid sample using the accepted sequence set.

2. The method of claim 1, wherein obtaining sequence data comprises single molecule sequencing.

3. The method of claim 2, wherein said single molecule sequencing comprises sequencing by a method chosen from single molecule sequencing by synthesis and ligation sequencing.

4. The method of claim 3, wherein said single molecule sequencing comprises real-time single molecule sequencing by synthesis.

5. The method of claim 3, wherein said single molecule sequencing comprises single molecule sequencing by synthesis by a method chosen from pyrosequencing, reversible terminator sequencing, and third-generation sequencing.

6. The method of claim 3, wherein said single molecule sequencing comprises nanopore sequencing.

7. The method of claim 1, wherein the circular nucleic acid molecule is formed by ligating the nucleic acid sample to the nucleic acid insert.

8. The method of claim 1, wherein the circular nucleic acid molecule is double-stranded.

9. The method of claim 1, wherein the nucleic acid sample is obtained from an RNA sample.

10. The method of claim 1, wherein the nucleic acid sample is obtained from a genomic DNA sample.

11. The method of claim 1, wherein the circular nucleic acid molecule comprises at least two insert-sample units.

12. The method of claim 1, wherein the nucleic acid insert comprises a promoter and synthesizing the product nucleic acid molecule comprises contacting the promoter with an RNA polymerase that recognizes the promoter followed by synthesizing a product nucleic acid molecule comprising ribonucleotide residues.

13. The method of claim 1, wherein the nucleic acid insert has a melting temperature ranging from 30° C. to 90° C.

14. The method of claim 1, wherein the nucleic acid insert has a length ranging from 14 to 200 nucleotide residues.

15. The method of claim 1, wherein the accepted sequence set is in a form chosen from a multi-element variable and a single data string comprising the sequence data of step (a) which has been processed to delete, overwrite, or omit repeats of the sequence of the nucleic acid sample rejected in step (c).

16. The method of claim 1, wherein the accepted sequence set is in the form of the multi-element variable of a type chosen from a list, array, hash, and matrix.

17. The method of claim 1, wherein at least two repeats of the sequence of the nucleic acid sample are accepted in step (c), and determining the sequence of the nucleic acid sample comprises determining a consensus sequence based on the at least two repeats of the sequence of the nucleic acid sample accepted in step (c).

18. The method of claim 17, wherein the consensus sequence comprises probabilistically represented bases at at least one position at which the at least two repeats of the sequence of the nucleic acid sample accepted in step (c) differ.

19. The method of claim 17, wherein at least three repeats of the sequence of the nucleic acid sample are accepted in step (c), and determining a consensus sequence comprises determining the majority vote of the at least three repeats of the sequence of the nucleic acid sample accepted in step (c).

20. The method of claim 17, wherein the consensus sequence is a position weight matrix.

21. The method of claim 17, wherein the consensus sequence is a flat sequence.

22. The method of claim 21, wherein the flat sequence comprises at least one ambiguity code.

23. The method of claim 17, wherein confidence levels are determined for the consensus sequence.

24. The method of claim 23, wherein the confidence levels are expressed in a form chosen from base frequency, information content, and Phred quality score.

25. The method of claim 23, wherein steps (a)-(e) of claim 1 are performed in real time, and the consensus sequence and confidence levels are updated in real time.

26. The method of claim 25, wherein the method is performed until a set minimum level of confidence at a preselected percentage of positions of the consensus sequence is achieved.

27. The method of claim 26, further comprising generating an alert when a preselected percentage of positions reach the set minimum level of confidence.

28. The method of claim 26, wherein the set minimum level of confidence is chosen from 90%, 95%, 99%, 99.5%, 99.9%, 99.95%, and 99.99% base call accuracy.

29. The method of claim 1, further comprising repeating the steps with at least one other nucleic acid sample from the same source, species, or strain as the nucleic acid sample that has a sequence that partially overlaps the sequence of the nucleic acid sample, thereby determining at least one other sequence, and assembling the at least one other sequence with the sequence of step (e) to form a contig.

30. The method of claim 1, wherein the scores of step (b) are used to estimate a confidence level of the sequence data of step (a) as a whole.

31. The method of claim 1, wherein calculating scores comprises determining the number of mismatches between the at least two inserts of the sequence data and the known sequence of the insert.

32. The method of claim 1, wherein calculating scores comprises determining the percent identity of the at least two inserts of the sequence data to the known sequence of the insert.

33. The method of claim 1, wherein calculating scores comprises performing an alignment between the at least two inserts of the sequence data and the known sequence of the insert.

34. The method of claim 33, wherein performing an alignment comprises using an algorithm chosen from BLAST, MEGABLAST, SmithWaterman alignment, and Needleman-Wunsch alignment.

35. The method of claim 1, wherein the scores are generated on a basis chosen from a count basis and a rate basis.

36. The method of claim 1, wherein accepting or rejecting at least two of the repeats of the sequence of the nucleic acid sample of the sequence data of step (a) comprises accepting those of the at least two repeats of the sequence of the nucleic acid sample that are immediately upstream or downstream of a sample insert sequence with a score greater than or equal to a pre-determined threshold, and rejecting those that are not.

* * * * *

SEQUENCE LISTING

<160> NUMBER OF SEQ ID NOS: 19

<210> SEQ ID NO 1
<211> LENGTH: 79
<212> TYPE: DNA
<213> ORGANISM: Artificial Sequence
<220> FEATURE:
<223> OTHER INFORMATION: Synthetic oligonucleotide

```
<400> SEQUENCE: 1
cgacttatgc atttggtatc tgcgctctgc atatttaaat ggaaggagat agttaaggat    60
aagggcagag cgcagatac                                                79

<210> SEQ ID NO 2
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 2
caaatgcata agtcgtgtct taccgggttg atagcggccg ctcggagaaa agaagttgga    60
tgatgcaacc cggtaagaca                                               80

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
ccttatcctt aactatctcc tt                                            22

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
tagcggccgc tcggagaaaa g                                             21

<210> SEQ ID NO 5
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (19)..(19)
<223> OTHER INFORMATION: m5c

<400> SEQUENCE: 5
agatgtggac ggggtgggcg gaggtgggtt ggggc                              35

<210> SEQ ID NO 6
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (24)..(24)
<223> OTHER INFORMATION: m5c
```

<400> SEQUENCE: 6
gcccaaccca cctccgccca ccccgtccaa catct            35

<210> SEQ ID NO 7
<211> LENGTH: 74
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (19)..(19)
<223> OTHER INFORMATION: m5c
<220> FEATURE:
<221> NAME/KEY: misc_feature
<222> LOCATION: (36)..(39)
<223> OTHER INFORMATION: n is a, c, g, or t
<220> FEATURE:
<221> NAME/KEY: modified_base
<222> LOCATION: (55)..(55)
<223> OTHER INFORMATION: m5c
<220> FEATURE:
<221> NAME/KEY: modified_base
<222> LOCATION: (64)..(64)
<223> OTHER INFORMATION: m5c

<400> SEQUENCE: 7
agatgtggac ggggtgggcg gaggtgggtt ggggcnnnng ccccaaccca cctccgccca    60
ccccgtccac atct                                                    74

<210> SEQ ID NO 8
<211> LENGTH: 74
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (19)..(19)
<223> OTHER INFORMATION: m5c
<220> FEATURE:
<221> NAME/KEY: misc_feature
<222> LOCATION: (36)..(39)
<223> OTHER INFORMATION: n is a, c, g, t or u
<220> FEATURE:
<221> NAME/KEY: modified_base
<222> LOCATION: (55)..(55)
<223> OTHER INFORMATION: m5c
<220> FEATURE:
<221> NAME/KEY: modified_base
<222> LOCATION: (64)..(64)
<223> OTHER INFORMATION: m5c

<400> SEQUENCE: 8
agatgtggac ggggtgggcg gaggtgggtt ggggunnnng uuuuaauuua uutucguuua    60
uuucguuuau atut                                                    74

<210> SEQ ID NO 9
<211> LENGTH: 74
<212> TYPE: DNA
<213> ORGANISM: Artificial Sequence
<220> FEATURE:

```
<223> OTHER INFORMATION: Synthetic oligonucleotide
<220> FEATURE:
<221> NAME/KEY: misc_feature
<222> LOCATION: (36)..(39)
<223> OTHER INFORMATION: n is a, c, g, or t

<400> SEQUENCE: 9
aaatataaac gaaataaacg aaaataaatt aaaacnnnna ccccaaccca cctccgccca      60
ccccgtccac atct                                                       74

<210> SEQ ID NO 10
<211> LENGTH: 39
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (36)..(39)
<223> OTHER INFORMATION: n is a, c, g, or t

<400> SEQUENCE: 10
agatgtggac ggggtgggcg gaggtgggtt ggggtnnnn                             39

<210> SEQ ID NO 11
<211> LENGTH: 39
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (36)..(39)
<223> OTHER INFORMATION: n is a, c, g, or t

<400> SEQUENCE: 11
aaatataaac gaaataaacg aaaataaatt aaaacnnnn                             39

<210> SEQ ID NO 12
<211> LENGTH: 74
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (36)..(39)
<223> OTHER INFORMATION: n is a, c, g, or t

<400> SEQUENCE: 12
agatgtggat ggggtgggtg gaggtgggtt ggggcnnnng cccaaccca cctctgccca       60 ccctgtccac atct                                                       74

<210> SEQ ID NO 13
<211> LENGTH: 74
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (36)..(39)
<223> OTHER INFORMATION: n is a, c, g, or t

<400> SEQUENCE: 13
agatgtggac agggtgggca gaggtgggtt ggggcnnnng cccaaccca cctccaccca       60 ccccatccac atct                                                       74
```

-continued

<210> SEQ ID NO 14
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 14
agatgtggat ggggtgggtg gaggtgggtt ggggc                          35

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 15
agatgtggac agggtgggca gaggtgggtt ggggc                          35

<210> SEQ ID NO 16
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (15)..(15)
<223> OTHER INFORMATION: n is 5-bromouracil
<220> FEATURE:
<221> NAME/KEY: misc_feature
<222> LOCATION: (30)..(30)
<223> OTHER INFORMATION: n is 5-bromouracil

<400> SEQUENCE: 16
agatgtggac ggggngggcg gaggtgggtn ggggc                          35

<210> SEQ ID NO 17
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (27)..(27)
<223> OTHER INFORMATION: n is 5-bromouracil

<400> SEQUENCE: 17
gccccaaccc acctccgccc accccgncca catct                          35

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
gccccaaccc acctccgccc gccccgtcca catct                          35

<210> SEQ ID NO 19
<211> LENGTH: 34
<212> TYPE: DNA
<213> ORGANISM: Artificial Sequence
<220> FEATURE:

-continued

```
<223> OTHER INFORMATION: Synthetic oligonucleotide

<400> SEQUENCE: 19
agatgtgggc ggggtgggcg gaggtgggtg gggc                                34
```